(12) United States Patent
Roberts et al.

(10) Patent No.: US 6,689,573 B1
(45) Date of Patent: *Feb. 10, 2004

(54) METHOD FOR SCREENING RESTRICTION ENDONUCLEASES

(75) Inventors: Richard J. Roberts, Wenham, MA (US); Devon R. Byrd, Germantown, MD (US); Richard D. Morgan, Middleton, MA (US); Jay Patti, Lynnfield, MA (US); Christopher J. Noren, Boxford, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/577,528

(22) Filed: May 24, 2000

Related U.S. Application Data

(60) Provisional application No. 60/135,541, filed on May 24, 1999.

(51) Int. Cl.$^7$ .................. G01N 33/573; C12N 15/74
(52) U.S. Cl. ............................ 435/7.4; 435/478
(58) Field of Search .................. 435/7.4, 478

(56) References Cited

U.S. PATENT DOCUMENTS

| | | | |
|---|---|---|---|
| 5,098,839 A | | 3/1992 | Polisson |
| 5,179,015 A | | 1/1993 | Wilson et al. |
| 5,180,673 A | * | 1/1993 | Wilson et al. |
| 5,278,060 A | | 1/1994 | Morgan |
| 5,866,422 A | * | 2/1999 | Wayne et al. |
| 6,383,770 B1 | * | 5/2002 | Roberts et al. |

FOREIGN PATENT DOCUMENTS

EP 0 456 356 A2 11/1991

OTHER PUBLICATIONS

Wilson (1991) Nucleic Acid Research 10: 2539–2566.*
Timinskas et al (1995) Gene 157:3–11.*
Pósfai et al (1989) Nucleic Acids Research 17: 2421–2435.*
Tomb et al (1997) Nature 388: 539–547.*
O'Connor and Timmis, Journal of Bacteriology, 169:4457–4462 (1987).
Bickle, in Nucleases [eds. Linn, S.M., Lloyd, S.L., and Roberts, R.J.], Cold Spring Harbor Laboratory Press, pp. 89–109 (1993).
Smith and Wilcox, J. Mol. Biol. 51:379–391 (1970).
Kelly and Smith, J. Mol. Biol. 51:393–409 (1970).
Middleton, et al., J. Virol. 10:42–50 (1972).
Roberts, et al., J. Mol. Biol., 91:121–123 (1975).
Schildkraut, "Screening For And Characterizing Restriction Endonucleases" in Genetic Engineering, Principles and Methods, vol. 6, pp. 117–140 Plenum Press (1984).
Roberts and Macelis, Nucl. Acids Res. 26:338–350 (1998).
Szomolayni, et al., Gene 10:219–225 (1980).
Mann, et al., Gene 3:97–112 (1978).
Kiss, et al., Nucl. Acids Res. 13:6403–6420 (1985).
Brooks, et al., Nucl. Acids Res. 17:979–997 (1989).
Elledge and Davies, Genes & Develop. 3:185–197 (1989).
Elledge, et al., PNAS USA 86:3689–3693 :(1989).
Dorner and Schildkraut, Nucl. Acids Res. 22:1068–1074 (1994).
Lubys, et al., Gene 141:85–89 (1994).
Withers, et al., Nucl. Acids Res. 20:6267–6273 (1992).
Lauster, et al., J. Mol. Biol. 206:305–312 (1989).
Wilson, Meth. Enzymol., 216:259–279 (1992).
Fleischmann, et al., Science 269:496–512 :(1995).
Fraser, et al., Science 270:397–403 (1995).
Bult, et al., Science 273:1058–1073 (1996).
Himmelreich, et al., Nucl. Acids Res. 24:4420–4449 (1996).
Kaneko, et al., DNA Res. 3:109–136 (1996).
Altschul, et al., J. Mol. Biol., 215:403–410 (1990).
Pearson and Lipman, PNAS USA 85:2444–2448 (1988).
Bolivar, et al., Gene 2:95–113 (1977).
Horiuchi and Inokuchi, Journal of Molecular Biology 23:217–224 (1967).
Nolling, et al., Nucleic Acids Res. 20:5047–5052 (1992).
Nolling, et al., Nucl. Acids Res. 20:6501–6507 (1992).
Roberts and Halford in Nucleases [eds. Linn, S.M., Lloyd, R.S., Roberts, R.J.] Cold Spring Harbor Press, pp. 35–88 (1993).

* cited by examiner

Primary Examiner—James Ketter
Assistant Examiner—Konstantina Katcheves
(74) Attorney, Agent, or Firm—Harriet M. Strimpel; Gregory D. Williams

(57) ABSTRACT

A method is provided for identifying a restriction endonuclease that includes: screening a target DNA sequence for the presence of known methylase sequence motifs, identifying any open reading frames which lie close to the screened methylase sequence motif and assaying the protein products of the open reading frames for restriction endonuclease activity.

8 Claims, 2 Drawing Sheets

FIG. 3

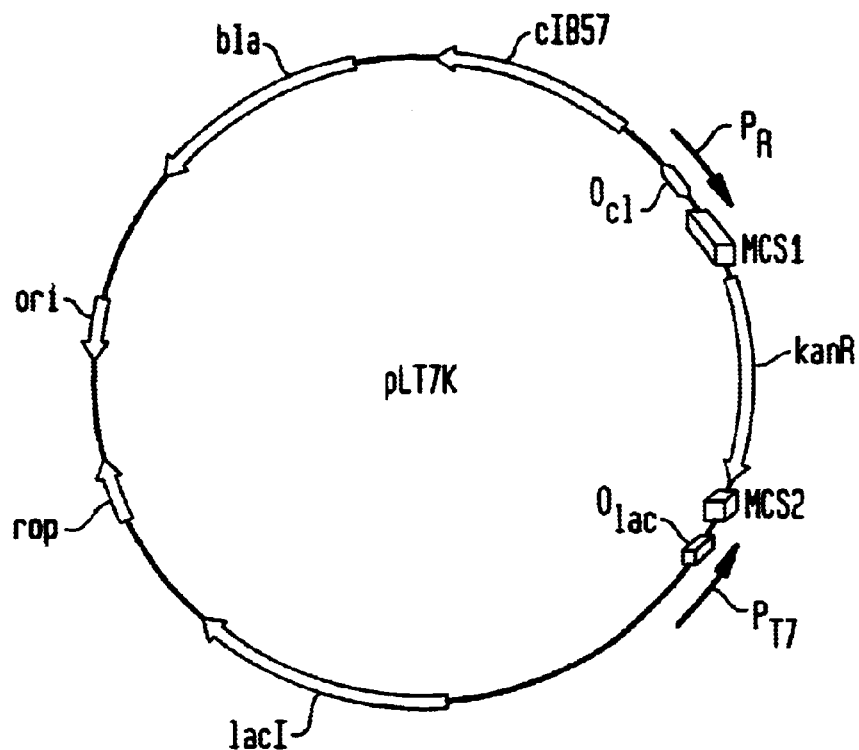

LEGEND

| | |
|---|---|
| cI857 | GENE ENCODING COLIPHAGE LAMBDA TRANSCRIPTIONAL REPRESSOR PROTEIN |
| $P_R$ | COLIPHAGE LAMBDA TRANSCRIPTIONAL PROMOTER SEQUENCE |
| $O_{cI}$ | cI REPRESSOR BINDING SITE |
| MCS1 | ONE OF TWO MULTIPLE CLONING SITES |
| kanR | GENE DETERMINING KANAMYCIN RESISTANCE |
| MCS2 | ONE OF TWO MULTIPLE CLONING SITES |
| $P_{T7}$ | COLIPHAGE T7 TRANSCRIPTIONAL PROMOTER SEQUENCE |
| $O_{lac}$ | LacI REPRESSOR BINDING SITE |
| lacI | GENE ENCODING E. COLI TRANSCRIPTIONAL REPRESSOR PROTEIN |
| rop | GENE ENCODING PLASMID REPLICATIVE CONTROL PROTEIN |
| ori | PLASMID REPLICATIVE ORIGIN |
| bla | GENE DETERMINING AMPICILLIN RESISTANCE |

METHOD FOR SCREENING RESTRICTION ENDONUCLEASES

This Non-Provisional Application is a Continuation-In-Part of U.S. application Ser. No. 09/486,356 filed Feb. 25, 2000 now U.S. Pat. No. 6,383,770 and claims the benefit of this Application as well as Provisional Application U.S. Ser. No. 60/135,541 filed May 24, 1999.

BACKGROUND OF THE INVENTION

The present invention relates to a novel method for screening and identifying restriction endonucleases based on the proximity of their genes to the genes of their cognate methylases. A similar method for identifying isoschizomers of known endonucleases, which isoschizomers possess a desired physical property is also provided. Related methods for producing and cloning such endonucleases or other cytotoxic proteins are provided, as are several novel *M. jannaschii* restriction endonucleases.

Nucleases are a class of enzymes which degrade or cut single- or double-stranded DNA. Restriction endonucleases are an important class of nucleases which recognize and bind to particular sequences of nucleotides (the 'recognition sequence') along the DNA molecule. Once bound, they cleave both strands of the molecule within, or to one side of, the recognition sequence. Different restriction endonucleases recognize different recognition sequences. Over two hundred restriction endonucleases with unique specificities have been identified among the many hundreds of bacterial and archaeal species that have been examined to date. Some have also been found to be encoded by eukaryotic viruses.

It is thought that in nature, restriction endonucleases, which comprise the first component of what are commonly referred to as restriction-modification ("RM") systems, play a protective role in the welfare of the host cell. They enable bacteria and archaea to resist infection by foreign DNA molecules like viruses and plasmids that would otherwise destroy or parasitize them. They impart resistance by cleaving invading foreign DNA molecules when the appropriate recognition sequence is present. The cleavage that takes place disables many of the infecting genes and renders the DNA susceptible to further degradation by non-specific endonucleases.

A second component of these bacterial and archaeal protective systems are the modification methylases. These enzymes are complementary to the restriction endonucleases and they provide the means by which bacteria and archaea are able to protect their own DNA from cleavage and distinguish it from foreign, infecting DNA. Usually, modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of the host cell is always fully modified by virtue of the activity of the modification methylase. It is therefore completely insensitive to the presence of the endogenous restriction endonuclease. It is only unmodified, and therefore identifiably foreign DNA, that is sensitive to restriction endonuclease recognition and cleavage.

There are three kinds of restriction systems. The Type I systems are complex. They recognize specific sequences, but cleave randomly with respect to that sequence (Bickle, T. A., Nucleases [eds. Linn, S. M., Lloyd, S. L., and Roberts, R. J.], Cold Spring Harbor Laboratory Press, pp. 89–109, (1993)). The Type III enzymes, of which only five have been characterized biochemically, recognize specific sequences, cleave at a precise point away from that sequence, but rarely give complete digestion (ibid). Neither of these two kinds of systems are suitable for genetic engineering, which is the sole province of the Type II systems. The latter recognize a specific sequence and cleave precisely either within or very close to that sequence. They typically only require Mg++ for their action.

The traditional approaches to screening for restriction endonucleases, pioneered by Roberts et al. and others in the early to mid 1970's (e.g. Smith, H. O. and Wilcox, K. W., *J. Mol. Biol.* 51:379–391 (1970); Kelly, T. J. Jr. and Smith, H. O., *J. Mol. Biol.* 51:393–409, (1970); Middleton, J. H. et al., *J. Virol.* 10:42–50 (1972); and Roberts, R. J. et al., *J. Mol. Biol.* 91:121–123, (1975)), was to grow small cultures of individual strains, prepare cell extracts and then test the crude cell extracts for their ability to produce specific fragments on small DNA molecules (see Schildkraut, I.S., "Screening for and Characterizing Restriction Endonucleases", in Genetic Engineering, Principles and Methods, Vol. 6, pp. 117–140, Plenum Press (1984)). Using this approach, about 12,000 strains have been screened worldwide to yield the current harvest of almost 3,000 restriction endonucleases (Roberts, R. J. and Macelis, D., *Nucl. Acids. Res.* 26:338–350 (1998)). Roughly, one in four of all strains examined, using a biochemical approach, shows the presence of a Type II restriction enzyme.

Beginning in 1978, investigators in a number of laboratories set about to clone the genes for some of the Type II restriction systems (Szomolanyi, I. et al., *Gene* 10:219–225 (1980)). This promised to be quite a successful enterprise because of the ease of selecting for methylase genes (Mann, M. B. et al., *Gene* 3:97–112 (1978); Kiss, A. M. et al., *Nucl. Acids. Res.* 13:6403–6420 (1985)). Basically, if an organism is known to contain a restriction system, then a shotgun of the organism's DNA can be made and the resulting mixed population of plasmids can be grown as a single, mixed culture. This mixed population of plasmid DNA's is then isolated, cleaved in vitro with the restriction enzyme, and only those plasmids that have both received and expressed the corresponding methylase gene, will survive the digestion. Upon retransformation, any cells that grow are greatly enriched for the presence of the methylase gene. Because the methylase and restriction enzyme genes are usually adjacent, this method can yield both genes. Sometimes a single round of selection is sufficient, but routinely two rounds of selection yield the required methylase gene with high efficiency. Only when expression of the methylase gene is poor or coexpression of flanking sequences is lethal does the selection fail. Various tricks and alternative cloning methods have been developed to overcome such limitations (e.g. Brooks, J. E. et al., *Nucl. Acids. Res.* 17:979–997 (1989); Wilson, G. G. and Meda, M. M., U.S. Pat. No. 5,179,015 (1993)).

As the skilled artisan will appreciate restriction endonucleases are cytotoxic products. In general, genes encoding cytotoxic products are extremely difficult to clone, even when care has been taken to remove sequences that might enable their expression in the plasmid host. Generation of their mRNA can be due to 'read-through' transcription that originates at some point on the plasmid other than the toxic locus. Absent an identifiable Shine-Dalgarno (SD) consensus sequence upstream of an initiator codon, translation of the toxic protein may be initiated by a cryptic ribosome binding site (RBS) (by definition, not fitting the SD consensus, and usually non-obvious), or abortive termination of an upstream ribosome-mRNA complex. Long mRNA concatamers can be generated from plasmid templates via 'rolling circle transcription'. This may increase and/or stabilize the mRNA of the toxic allele, so that even rare translational initiation events can generate enough protein to impact cell viability negatively.

Attempting to clone a toxic gene into a plasmid designed to facilitate high expression is, in many cases, futile. Transcriptional repressors are often employed to down-regulate expression, and typically act by interfering with productive transcription. This type of regulation is dependent upon: 1) the molar ratio of repressor protein to its cognate binding site (operator), and 2) the affinity of the repressor protein for the operator sequence. In no case is it reasonable to expect 100% of the operator sites to be occupied 100% of the time. Thus, some expression of a cloned gene is unavoidable, creating a powerful selective pressure against cells that faithfully replicate the lethal gene. Those cells in which expression of the toxic gene has been mutagenically inactivated survive.

Genes encoding cytotoxic products must be actively and constitutively down-regulated, and any adventitious expression eliminated at both the transcriptional and translational levels.

This may be accomplished through the action of antisense RNAs (asRNA). The asRNA base pairs with a segment of mRNA and presumably inhibits translational initiation or elongation. The use of opposing promoters to modulate expression of a gene encoding a potentially toxic protein has been reported (O'Connor and Timmis, *J. Bacteriol.* 169(10):4457–4462 (1987)). Their system employed the endogenous *E. coli* RNA polymerase ("RNAP"), with the sense RNA (SRNA) generated from the λ-derived $P_L$ promoter, and asRNA initiating at the *E. coli* $P_{lac}$ promoter. Operator sequences for repressor proteins normally associated with these promoters, namely cI and LacI, were also present on the high copy plasmid (pUC8/18) backbone. A second copy of the LacI operator was inserted between $P_L$ and the gene of interest. The alleles encoding the cI857 and LacI repressor proteins were not part of the plasmid, but were provided either from the chromosome (cI857λ prophage) or on the low copy plasmid pACYC184 (lacI).

This approach to cloning a cytotoxic gene, however, suffers from several shortcomings:

1) a high copy replicon significantly raises the dosage of the toxic allele, increasing the likelihood for undesired expression;
2) placement of operator sequences on a high copy replicon, while the genes encoding the repressor proteins are present at substantially lower copy number, does not provide optimal repression;
3) strong repression of gene expression and elective induction of gene expression are mutually exclusive.

While the idea of using opposing promoters to modulate gene expression has been previously demonstrated (Elledge and Davis, *Genes & Develop.* 3:185–197 (1988)), it has not been demonstrated as a successful method using a toxic gene. The Elledge, et al. system relies upon conditional expression of a gene encoding spectinomycin resistance. This approach proved to be a useful genetic selection for genes encoding proteins capable of exhibiting transcriptional repressor-like activity (Elledge et al., *PNAS USA* 86:3689–3693 (1989); Dorner and Schildkraut, *Nucl. Acid. Res.* 22(6):1068–1074 (1994)). These studies showed that transcriptional inactivation of a gene can be achieved with an antisense promoter.

It is imperative that stable clones of desired loci (including those encoding cytotoxic products) be established in the context of an inducible expression system, such as an *E. coli* expression system, for the following reasons:

a) to generate a physical archive of single genes encoding potentially novel biochemical activities (as opposed to phage or cosmid constructs containing many genes);

b) to allow for rapid and facile characterization and/or manipulation of the entire allele;

c) and to move rapidly from discovery to production.

It would therefore be desirable to develop a method for cloning genes encoding cytotoxic products, including restriction endonucleases, or other genes which cannot be stably cloned by traditional methods, in order to enable the generation of the above-mentioned archive.

Nonetheless, as a result of current cloning methods, more than 100 systems have been cloned and many have been sequenced (Wilson, G. G., *Nucl. Acids. Res.* 19:2539–2566 (1991)). Several conclusions have emerged. First, genes for restriction endonucleases that recognize unique sequences are usually different from one another and their sequences are unique within GenBank. Typically, the only time when similarity has been found between restriction enzyme gene sequences is when the two enzymes are isoschizomers or have closely related recognition sequences; i.e. they recognize exactly the same sequence, but come from different microorganisms (e.g. Lubys, A. et al., *Gene* 141:85–89 (1994); Withers, B. E. et al., *Nucl. Acids. Res.* 20:6267–6273 (1992)). Second, among methylase gene sequences there is very strong similarity between enzymes that form 5-methylcytosine (m5C), such that they can readily be recognized by pattern matching algorithms (Posfai, J. et al., *Nucleic Acids. Res.* 17:2421–2435 (1989); Lauster, R. et al., *J. Mol. Biol.* 206:305–312 (1989)). The genes for methylases that form N6-methyladenine (N6A) or N4-methylcytosine (N4C) are also related to one another, but show fewer well-conserved similarities. At least three subfamilies of sequences can be recognized (Wilson, G. G., *Meth. Enzymol.* 216:259–279 (1992), Timinskas et al. *Gene* 157: 3–11 (1995)). In this case, pattern matching algorithms do fairly well, but cannot provide conclusive evidence whether a newly sequenced gene encodes an N6A or an N4C methyltransferase. Third, and most significant, for virtually all known RM systems that have so far been cloned, the methylase gene and the restriction enzyme gene lie either adjacent or extremely close to one another (Wilson, G. G., *Nucl. Acids. Res.* 19:2539–2566 (1991)).

Within the last year, sequences have become available for many complete bacterial and archaeal genomes, including: *Haemophilus influenzae* (Fleischmann, R. D. et al., *Science* 269:496–512 (1995)), *Mycoplasma genitalia* (Fraser, C. M. et al., *Science* 270:397–403 (1995)), *Methanococcus jannaschii* (Bult, C. J. et al., *Science* 273:1058–1073 (1996), *Mycoplasma pneumoniae* (Himmelreich, R. et al., *Nucl. Acids. Res.* 24:4420–4449 (1996)) and *Synechocystis* species (Kaneko, T. et al., *DNA Res.* 3:109–136 (1996)). *H. influenzae* and *M. jannaschii* were each known to encode two Type II RM systems (Roberts, R. J. and Macelis, D. M., supra (1998)). The complete sequences of their genomes have revealed a remarkable fact. In each case, these genomes appear to contain multiple RM systems many of which have never been detected biochemically. The results of computer analysis of these sequences is compared with the biochemical results shown in Table 1:

TABLE 1

| RM Systems Organisms | RM Systems Detected by Computer | Detected Biochemically |
|---|---|---|
| H. influenzae | 8 | 2 |
| M. genitalia | 2 | not tested |
| M. jannaschii | 12 | 2 |
| M. pneumoniae | 4 | not tested |
| Synechocystis species | 4 | not tested |

As mentioned earlier, among Type II restriction enzymes there are now more than two hundred different specificities present. Table 2 shows the kind of sequence patterns that are currently known to be recognized by restriction endonucleases. It lists the number of specific examples of each presently in the database, compared with the theoretical number based on all possible sequence combinations.

In column 1 of this table, the pattern representation, n', signifies the complement of n. Thus nnn'n' in the first entry is used to represent the 16 possible tetranucleotide palindromes AATT, ACGT, AGCT etc.

It is clear that for some types of patterns, such as the simple hexanucleotide and tetranucleotide palindromes, we are very close to having all possible such enzymes. However, for many of the other patterns we are a long way away from the theoretically possible number. This suggests that there are many more specificities waiting to be discovered.

Accordingly, it would be desirable to provide an alternative method for screening for restriction endonucleases which would overcome the limitations associated with the traditional biochemical methods described above. Such an alternative method would facilitate the identification, characterization, and cloning of heretofore unknown restriction endonucleases as well as isoschizomers of known restriction endonucleases.

TABLE 2

Sequence patterns recognized by Type II restriction enzymes
Specific Example

| Pattern | Rec. Sequence | Enzyme | Observed | Possible |
|---|---|---|---|---|
| nnn'n' | AATT | TspEl | 14 | 16 |
| nnnn'n'n' | AACGTT | Acll | 55 | 64 |
| nnnnn'n'n'n' | ATTTAAAT | Swal | 9 | 256 |
| nnnnn | ACGGC | Bcefl | 18 | 1024 |
| nnnnnn | ACCTGC | BspMl | 25 | 4096 |
| nnNn'n' | ACNGT | Tsp4Cl | 7 | 16 |
| nDnn'Hn' | GDGCHC | Sdul | 1 | 16 |
| nKnnnn | GKGCCC | Bmgl | 1 | 1024 |
| nMnn'Kn' | CMGCKG | NspBll | 1 | 16 |
| nnBNNNNNVn'n' | GABNNNNNVTC | Hin4l | 1 | 16 |
| nnMKn'n' | GTMKAC | Accl | 1 | 16 |
| nnnn | CCGC | Acil | 2 | 256 |
| nnNNn'n' | CCNNGG | Secl | 3 | 16 |
| nnnNn'n'n' | CCTNAGG | Saul | 3 | 64 |
| nnnNnnn | CACCTGC | UbaEl | 3 | 4096 |
| nnnNNNn'n'n' | CACNNNGTG | Dralll | 3 | 64 |
| nnnNNNNn'n'n'n' | GAANNNNTTC | Xmnl | 3 | 64 |
| nnnNNNNNn'n'n' | CCANNNNNTGG | PflMl | 6 | 64 |
| nnNNNNNNn'n' | CCNNNNNNGG | BsiYl | 2 | 16 |
| nnnNNNNNNn'n'n' | ACCNNNNNNGGT | HgiEll | 3 | 64 |
| nnnnNNNNNn'n'n'n' | GGCCNNNNNGGCC | Sfil | 1 | 256 |
| nnNNNNNnnnn | ACNNNNNCTCC | BsaXl | 2 | 4096 |
| nnnNNNNNNNnn | CGANNNNNNTGC | Bcgl | 3 | 1024 |
| nnnnNNNNNNNnnn | GAACNNNNNNTCC | UbaDl | 1 | 16384 |
| nnnNNNNNNNNNn'n'n' | CCANNNNNNNNNTGG | Xcml | 1 | 64 |
| nnNNNNnnnYn | ACNNNNGTAYC | Bael | 1 | 4096 |
| nnnRnn | CAARCA | Tth111ll | 2 | 1024 |
| nnnWn'n'n' | ACCWGGT | SexAl | 4 | 64 |
| nnRYn'n' | ACRYGT | Aflll | 4 | 16 |
| nnSn'n' | CCSGG | Caull | 3 | 16 |
| nnWn'n' | CCWGG | EcoRll | 4 | 16 |
| nnWWn'n' | CCWWGG | Styl | 1 | 16 |
| nnYNNNNRn'n' | CAYNNNNRTG | Msll | 1 | 16 |
| nnyRn'n' | CTYRAG | Smll | 3 | 16 |
| nRnn'Yn' | GRCGYC | Acyl | 2 | 16 |
| nRnnn'n'Yn' | CRCCGGYG | SgrAl | 1 | 64 |
| nWnn'Wn' | GWGCWC | HgiAl | 1 | 16 |
| nYnn'Rn' | CYCGRG | Aval | 1 | 16 |
| Rnn'Y | RGCY | CviJl | 1 | 4 |
| Rnnn'n'Y | RAATTY | Apol | 5 | 16 |
| RnnNn'n'Y | RGGNCCY | Drall | 1 | 16 |
| RnnWn'n'Y | RGGWCCY | PpuMl | 1 | 16 |
| Wnnn'n'W | WCCGGW | Betl | 3 | 16 |
| Ynn'n'R | YACGTR | BsaAl | 2 | 16 |
| Ynnnnn | CGGCCR | Gdill | 1 | 1024 |

SUMMARY OF THE INVENTION

In accordance with one embodiment of the present invention, a novel method for screening for restriction endonucleases is provided. This method has been successfully employed and may be used to identify heretofore unknown restriction endonucleases as well as isoschizomers of known restriction endonucleases, such isoschizomers possessing a desired physical property, such as thermostability. This novel method will also facilitate the characterization, cloning and production of newly identified restriction endonucleases and isoschizomers.

More specifically, in its broadest application the present invention comprises the following steps:
  (a) screening a target DNA sequence for the presence of known DNA methylase sequences and motifs characteristic of DNA methylases;
  (b) identifying open reading frames which lie close to the DNA methylase sequence of step (a); and
  (c) analyzing the protein product of the open reading frame of step (b) for endonuclease activity.

Once a new restriction endonuclease or isoschizomer has been identified in accordance with the above-outlined methodology, the restriction endonuclease so identified may be produced in accordance with standard protein purification techniques or by recombinant DNA techniques.

Several novel restriction endonucleases isolated from *M. jannaschii* using the methods of the present invention are also provided, including MjaII, which is a thermostable isoschizomer of Sau961, MjaIII, which is a thermostable isoschizomer of MboI, and MjaIV, a new specificity recognizing GTNNAC.

Also provided by the present invention is a novel method for stably cloning DNA sequences which might otherwise be unstable because the products encoded are toxic. One example provided has a stable, inducible clone encoding the normally toxic restriction endonuclease PadI in the absence of a protective methylase.

BRIEF DESCRIPTION OF THE DRAWINGS

FIG. 3 is a diagram depicting the vector pLT7K used in the stable cloning of genes encoding cytotoxic proteins of Examples IX and X.

DETAILED DESCRIPTION OF THE INVENTION

Figure 1:
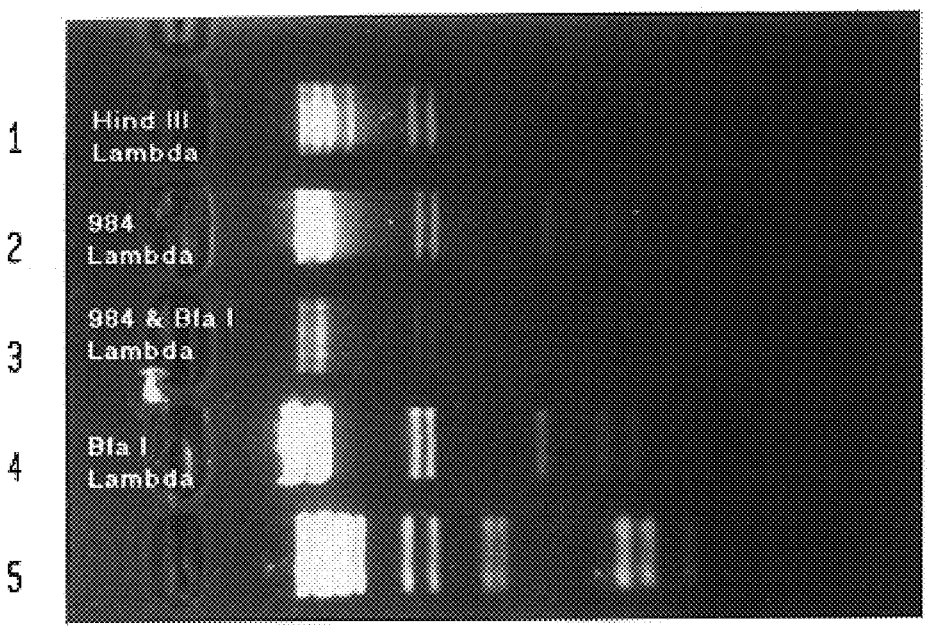
FIG. 1 shows the agarose gel electrophoresis of DNAs digested by the transcription/translation product of the MJ0984 open reading frame from *M. jannaschii* and BfaI (recognition sequence CTAG). Lane 1:BstNI/pBR322 markers; Lane 2: bacteriophage λ DNA digested with BfaI; Lane 3: double digest of bacteriophage λ DNA with BfaI and the transcription/translation product from MJ0984; Lane 4: bacteriophage λ DNA digested with the transcription/translation product from MJ0984; Lane 5: HindIII/bacteriophage λ DNA markers.

In accordance with one preferred embodiment of the present invention, there is provided a novel method for identifying a restriction endonuclease. The first step of this method is to compile a database of DNA sequences that encode either a DNA methylase or a restriction enzyme. This can be accomplished by searching GenBank for coding sequences that carry the annotation "methylase", "methyltransferase", "modification methylase", "restriction endonuclease" or "restriction enzyme". All such sequences are collected and used as the master database of restriction enzyme and methylase gene sequences, the "RM sequence database". If desired, and if available, then other DNA sequences known to encode DNA methylases or restriction endonucleases, not present in GenBank, can be included in this master collection.

The second step is to take the new target sequence, say that of a bacterial genome, and compare each open reading frame present in that sequence against the RM sequence database. Preferably, this is accomplished using the program BLAST (Altschul, S. F., Gish, W., Miller, W., Myers, E. W. and Lipman, D. *J. Mol. Biol.* 215: 403–410 (1990)) or other comparable searching routines, such as FASTA (Pearson, W. and Lipman, D. *Proc. Natl. Acad. Sci. USA* 85: 2444–2448 (1988)). Each time that a significant match is found between an open reading frame in the target sequence and a known gene in the RM sequence database, it is examined more carefully. If the match is to a restriction endonuclease gene, then that open reading frame is likely to encode a restriction enzyme and it can be investigated biochemically as detailed below. Where the matches are to DNA methylase genes the matches are examined to see if the short sequence motifs characteristic of cytosine-5 methylases (Posfai, J. et al., *Nucleic Acids. Res.* 17:2421–2435 (1989); Lauster, R. et al., *J. Mol. Biol.* 206:305–312 (1989)) or those characteristic of N4C- or N6A-methylases (Wilson, G. G., *Meth. Enzymol.* 216:259–279 (1992), Timinskas et al. *Gene* 157: 3–11 (1995)) are present. If they are, then it is concluded that the new open reading frame in the target sequence is likely to encode a DNA methylase. Because DNA methylases and their cognate restriction endonucleases have usually been found to be encoded close to one another (Wilson, G. G., *Nucl. Acids. Res.* 19:2539–2566 (1991)), it is of particular interest to examine the open reading frames that flank this methylase gene to see if they can be considered new restriction enzyme gene candidates.

The open reading frames that flank the newly identified methylase gene are preferably first checked to see if they have homologs in the RM sequence database. If one shows even weak similarity to a known restriction enzyme gene, then it is considered to be a prime candidate to encode a new restriction endonuclease of the same specificity and it can be characterized biochemically as described below. If the flanking sequences show no similarity to any sequence in the RM sequence database, then they are compared with the entire GenBank database to see it a match can be detected to some other sequence. Again BLAST can be used for this purpose. If they show a match to some gene of known function, that is not a methylase or a restriction enzyme, then they can be eliminated as a prime candidate for the restriction enzyme gene, although it cannot be rigorously excluded in the absence of direct biochemical evidence. If both flanking genes have good matches in GenBank, then the original methylase gene is considered to be an orphan methylase (i.e., a methylase which is not associated with a cognate restriction endonuclease) that does not form part of a restriction/modification system. In some instances, however, (see, Example VI), the restriction endonuclease gene may be separated from its cognate methylase by an intervening ORF, thus necessitating analysis of ORFs upstream and downstream from the ORF flanking the methylase gene. In this situation, adjacent ORFs greater than about 100 amino acids (approximately 300 nucleotides) should be examined. If this does not yield any candidate genes, the examination should continue upstream and downstream to the next ORF of greater than about 100 amino acids. This process should continue up to about 3 kb on either side of the methylase gene. If either one or both flanking open reading frames are unique (i.e. have no homologs in GenBank) then they become candidates for new restriction enzyme genes.

Once an open reading frame has been identified that is a candidate for a restriction enzyme gene, a purely in vitro procedure is preferably used to prepare a small sample of the protein product of that open reading frame followed by testing of the protein product for restriction enzyme activity, again in vitro. In one preferred embodiment, whole genomic DNA from the microorganism is prepared, and two PCR primers are synthesized. One primer corresponds to a region that lies downstream (3') of the stop codon of the open reading frame, contains about 20 nucleotides complementary to the coding strand and an additional 10–15 nucleotides that contain a restriction enzyme recognition site not found in the gene itself, in case later cloning is required. This primer which is typically 30–35 nucleotides long, and is designed to copy the non-coding strand.

The second primer is designed to produce the coding strand. This second primer contains, close to its 5' prime end, a restriction enzyme recognition site not found in the gene, followed by a promoter site for a polymerase such as T7 RNA polymerase, a ribosome binding site appropriate for the translation system being used in the later step, and positioned so that translation will begin with the first start codon of the open reading frame that is the candidate for the restriction enzyme gene. Typically, about 20 additional nucleotides are present at the 3' end of this primer that correspond to the first few codons of the open reading frame.

These two primers are then used in a standard amplification procedure such as the polymerase chain reaction (PCR) so that a linear piece of DNA is produced, which contains a T7 promoter, a ribosome biriding site, and the complete open reading frame that is the candidate for the restriction enzyme gene. This PCR product is used as a template for transcription in vitro by T7 RNA polymerase. This results in the production of a large amount of RNA containing the complete coding sequence for the candidate open reading frame. Either with or without further purification the RNA template produced is then used as a template for translation in vitro using a standard commercial translation system.

One preferred method of assaying for the presence of endonuclease activity is in vitro transcription-translation using the rabbit reticulocyte system. Another preferred method of assaying for such endonuclease activity is the *E. coli* S-30 transcription-translation system.

In accordance with the present invention, it has been found that a particularly preferred method for assaying for thermophilic endonuclease activity is the wheat germ based translational system.

When assaying for endonuclease activity it is often necessary to incubate the translation product and substrate DNA at a temperature that mimics the normal living conditions of the organism from which the gene originated. When assaying a translation product of an ORF that was amplified from a thermophilic organism's genomic DNA the assay is usually incubated at temperatures ranging from 50° C. to 80° C. It was found that at temperatures above 50° C. the reticulocyte translational mix begins to congeal and endonuclease activity is hard to detect. Although thermophilic endonucleases have been identified using reticulocyte based translations, the wheat germ translation mix does not congeal when heated in the same way and hence is a more practical assay particularly for thermophilic endonucleases.

Following translation, during which time a small amount of the protein product from the candidate open reading frame will have been produced, the entire translation mix is assayed for the presence of the restriction enzyme using well established techniques. (Schildkraut, "Screening for and Characterizing Restriction Endonucleases", in Genetic Engineering, Principals and Methods, Vol 6, pp. 117–140, Plenum Press (1984)). This may be accomplished, for example, by taking a small portion of the translation mix and incubating it with several substrate DNAs such as those from bacteriophage λ, bacteriophage T7, Adenovirus-2, etc. that are likely to contain one or more recognition sites for the restriction enzyme. Typically, the assays are allowed to run from 30 minutes to 16 hours. The whole mix is then applied to an agarose gel where DNA fragments separate according to size. If a restriction enzyme is present in the translation mix, then usually that restriction enzyme will cleave one of the test substrate DNAs, leading to the banding pattern that is typical of restriction endonucleases. If bands are detected, then the specificity of the restriction enzyme can be determined using standard procedures. (Schildkraut, supra (1984)).

Another preferred method for identifying the restriction enzyme encoded by a candidate gene involves first cloning the candidate open reading frame, together with its adjacent methylase gene into an appropriate host cell such as *E. coli*. For this purpose, PCR primers may be chosen so as to amplify the complete coding sequences for both methylase and restriction enzyme genes. These may be placed into a standard expression vector such as pUC19, and the resulting transformants would be tested for restriction endonuclease using standard procedures. Briefly, a small sample of each clone is grown. The cells may be harvested and sonicated to prepare a crude cell lysate. Following centrifugation to remove cell debris, the supernatant may be tested for restriction endonuclease activity by incubation of small samples with various DNAs as described above.

It is conceivable that either the methylase gene and/or the endonuclease gene might be lethal in the host cell, in which case the frequency of transformants from the PCR product, would be abnormally low. In those circumstances, another approach is possible. Specifically, PCR may be used to amplify the methylase gene in the absence of its flanking sequences, and this gene may be cloned into an appropriate host cell such as *E. coli*. In this case, the transformants may be tested for methylase activity using a standard assay in which a crude extract from the clone and an appropriate DNA substrate such as those from bacteriophage λ, bacteriophage T7, Adenovirus-2, etc. would be incubated with [$^3$H]-S-adenosylmethionine. The incorporation of [$^3$H] into DNA may then be monitored by scintillation counting. The successful cloning of an active methylase gene may be detected if the crude extract can transfer $^3$H counts into DNA. If methylase clones are successfully obtained, then such clones may be expected to protect the host *E. coli* DNA against the possible deleterious action of the restriction endonuclease. An appropriate host cell which harbors the methylase clone may then be used as a recipient in a second cloning experiment, to obtain the endonuclease gene. This may be obtained by its amplification by PCR and cloning into a second compatible vector plasmid. As before, transformants may be tested for the presence of active restriction endonuclease.

The present invention also relates to multipurpose cloning vectors and their use in cloning and/or in vitro and/or in vivo transcription and/or translation of nucleic acid segments that may be cytotoxic and/or may produce cytotoxic products.

(1) A nucleic acid segment constituting an ORF is isolated and/or acquired by standard molecular biological methods. This may be undertaken so as to either maintain, or selectively alter the native sequence context of the coding region. The native sequence of the first (ATG, GTG, or TTG), or last (TAA, TAG, TGA) codon may be maintained or selectively altered in order to modulate translational efficiency, and/or provide for translational fusion.

In a preferred method, a nucleic acid segment (ORF) is recombined by standard molecular cloning techniques into a plasmid having the following properties:

i) oppositely oriented (convergent) transcriptional promoters, providing for sense-, anti-sense, and/or bidirectional transcription, flanking the inserted DNA segment. Preferably, the promoters will be cognate substrates for nonidentical RNAPs, and will not functionally substitute for RNAPs for which they are not cognate substrates. To provide for transcription of a particular strand of the inserted DNA segment, the vector preferably possesses a promoter that is a substrate for a host cell RNAP, such as the E. coli τ70 RNAP promoter, $\lambda P_L$ or $P_R$. In addition, to provide for transcription of the complementary strand of the inserted DNA segment, the vector of the present invention preferably possesses a promoter that is a substrate for a non-host cell RNAP, such as bacteriophage T7 RNAP promoter, $P_{T7}$.

ii) the opposing promoters will contain sequences (operators) providing for binding of transcriptional repressor proteins (repressors). Preferably, the operators will be cognate ligands for nonidentical repressors, and will not functionally substitute for repressors for which they are not cognate ligands. To provide for transcriptional repression of a particular sequence of the inserted DNA segment, the vector preferably possesses an operator, such as $O_{lac}$, that is a ligand for a repressor such as E. coli LacI. In addition, to provide for transcriptional repression of the complementary sequence of the inserted DNA segment, the vector preferably possesses an operator, such as $O_{cl}$, that is a ligand for a repressor, such as bacteriophage $\lambda$cl857.

iii) to modify the degree of transcription of a particular sequence of the inserted DNA segment, the cognate operator:repressor binding interactions may be selectively and independently manipulated. Preferably, conditions that affect one operator:repressor binding interaction, will not detectably affect the other, and vice versa. To alleviate transcriptional repression via destabilization of an operator:repressor binding interaction, such as $O_{lac}$:$P_{T7}$, a synthetic chemical compound, such as isopropyl-thio-β-D-galactopyranoside (IPTG) is used. In addition, to alleviate transcriptional repression via destabilization of an operator:repressor binding interaction, such as $O_{cl}$:cl857, permissive and non-permissive temperatures are employed.

iv) to provide for its selective maintenance in cultured cells, the vector preferably possesses a genetic element specifying an antibiotic resistance phenotype, such as a β-lactamase allele.

v) to provide for the persistence of a desired embodiment, the vector preferably possesses genetic elements capable of directing its episomal and/or intrachromosomal replication, such as the replicative origin of pBR322 (Bolivar, et al., *Gene*, 2:95–113 (1977)).

One especially preferred plasmid is pLT7K (see FIG. 3). The segment encoding replicative functions (encoded by rop and orI) is derived from pBR322 (Bolivar, et al., supra (1977)). The gene encoding β-lactamase (bla) confers ampicillin resistance, and has been altered to remove a recognition site for the PstI restriction endonuclease. The gene encoding kanamycin resistance is flanked by restriction sites suitable for cloning. The cl857 gene encodes a mutant form of the repressor protein, cl857 (Horiuchi and Inokuchi, *Journal of Molecular Biology*, 23(2):217–224 (1967)). The cl857 protein conditionally binds to DNA sequences (the cl operators, or $O_{cl}$) that overlap $P_R$ (bacteriophage λ major rightward promoter). The lad gene encodes a repressor protein, LacI, that conditionally binds a DNA sequence (the lac operator, or $O_{lac}$) which has been constructed to overlap $P_{T7}$ (bacteriophage T7 RNA polymerase transcriptional promoter). The segment containing λ cl857 and $P_R$ was subcloned from the pGW7 (Geoffrey Wilson, New England Biolabs, Inc.) derivative, pJIH1 (gift of R. E. Webster, Duke University).

All of the genetic elements mentioned above are specified by sequences present on the plasmid. Transcription from $P_R$ proceeds towards $P_{T7}$, whereas transcription from $P_{T7}$ proceeds towards $P_R$. Transcription from $P_R$ is dependent upon the endogenous E. coli RNA polymerase, whereas from $P_{T7}$ it is dependent upon expression of an RNAP derived from bacteriophage T7.

(2) The resulting construction is transformed into an appropriate host cell such as E. coli strain under conditions intended to disallow undesired expression of the insert DNA, as specified in Example IX. Transformants are randomly selected for small-scale plasmid DNA preparation. The plasmid DNA is analyzed by restriction enzyme digestion for a banding pattern consistent with the desired clone. A sampling of clones exhibiting the appropriate restriction pattern is sequenced across the insertion site and compared to the original database entry.

Clones that pass these examinations are transformed into an E. coli strain carrying two distinct RNAPs whose relative transcriptional efficiency can be simultaneously and independently modulated in an elective manner. Transformation and colony selection are carried out as above. Selected colonies are grown in liquid culture conditions intended to disallow expression of the insert DNA. Culture conditions may be subsequently altered so as to favor expression of the insert DNA. (See, e.g., Example IX.)

In a particularly preferred embodiment, the cl857 protein, which is a temperature sensitive mutant of the cl repressor, is used to control $P_R$-directed transcription by the host RNAP. The degree of $O_{cl}$ occupation by cl857 can be modulated by the temperature of the bacterial culture conditions. At ~30° C. (permissive temperature), cl857 can bind $O_{cl}$ and effectively repress transcription from $P_R$. However at ~37° C. (non-permissive), cl857 cannot stably bind, and transcription from $P_R$ by the host RNAP is enabled.

In one preferred embodiment, a plasmid host strain carrying genetic elements allowing for elective induction of an exogenous RNAP, such as E. coli strain ER2566 is used. ER2566 carries a gene encoding T7 RNAP (T7g1) inserted into the chromosomal lacZ locus, expression of which is repressed by LacI. Addition of IPTG to an ER2566-pLT7(x) (wherein "x" designates a specific construction derived from pLT7K) culture will: (1) alleviate LacI mediated repression of the lac operon and promote expression of T7 RNAP by the host RNAP; and (2) alleviate LacI occupation of the plasmid-borne $O_{lac}$ site, thereby enabling transcription from $P_{T7}$ by T7 RNAP.

The $O_{lac}$: LacI interaction is not significantly affected by temperature, nor is the $O_{cI}$: cI857 interaction affected by the presence of IPTG. In the most preferred embodiment, operator:repressor interactions such as these can be simultaneously and independently manipulated, subsequently affecting transcriptional efficiency from respective promoters, such as $P_{T7}$ and $P_R$. Since the DNA sequences encoding the repressor proteins and operators are in cis, the molar ratio of repressor alleles to their respective operator sites is essentially equivalent to their normal chromosomal ratio. Thus, one may expect the desired repressor:operator interactions to quantitatively reflect wild-type interactions.

The location and relative orientation of the plasmid-borne repressor alleles enables very tight regulation of expression from the desired promoter. For instance, in the unanticipated event that LacI levels drop below some critical threshold for $O_{lac}$ occupation (under culture conditions intended to favor expression from $P_R$, but not $P_{T7}$), lacI could be expressed by virtue of readthrough transcription originating from $P_R$, in addition to its own promoter. This would increase the level of lacI transcript and concomitant expression of the LacI repressor protein. The same scenario applies to cI857 expression from $P_{T7}$ (see FIG. 3). Thus, strong positive regulation of the desired repressor operator interaction has been built in to the system.

If desired, expression can be further controlled by either eliminating, or independently inhibiting either of the RNAPs. T7 RNAP, for example, can be physically excluded by using an E. coli strain that does not encode it. If a T7 RNAP allele is present, its adventitious expression can be mitigated by including a plasmid encoding coliphage T7 lysozyme, such as pLysP (gift of W. F. Studier, Brookhaven National Laboratory). T7 lysozyme interacts stoichiometrically with T7 RNAP and prevents the polymerase from effectively extending transcripts from $P_{T7}$. Addition of IPTG to the culture medium promotes the generation of sufficient amounts of T7 RNAP to overcome inhibition by T7 lysozyme. E. coli RNAP can be inhibited by the addition of the antibiotic rifampicin to the culture medium. T7 RNAP is not sensitive to ritampicin, nor is E. coli. RNAP known to be affected by either IPTG or T7 lysozyme. Thus, transcription catalyzed by the respective RNAPs can be simultaneously and independently modulated.

(3) Cultures are harvested by centrifugation and sonicated to produce a crude lysate. Following centrifugation to remove cell debris, the supernatant is tested for biochemical activity, as appropriate. In the case of restriction endonuclease activity, the supernatant is incubated with various DNAs as described above.

The stabilization of a nucleic acid segment in a vector such as pLT7K allows for sequence verification, mutagenesis, and expression. This solves the following shortcomings of in vitro transcription/translation (txn/tln) of a comparatively ephemeral PCR product:

(a) A negative result cannot be unambiguously interpreted as the absence of a desired biochemical activity because: i) the lack of an internal positive control precludes discrimination between a technical failure and no activity; ii) the protein may not be sufficiently stable to survive the assay; iii) the protein may not be produced in sufficient quantity to generate a detectable signal in the assay; iv) the protein may not have sufficient specific activity to generate a detectable signal in the assay; v) the protein may not be active in the txn/tln extract; vi) there may be inactivating mutations in the genomic DNA from which the candidate PCR product is amplified, and; vii) propagation of early PCR errors may negatively affect signal detection in the assay;

(b) The PCR product is consumed as a function of the assay and must be regenerated as needed, with two significant consequences: i) it consumes genomic DNA (the source of all the candidate loci), which can be problematic if the DNA is difficult to obtain as has been the case for *Methanococcus jannaschii*; ii) more importantly, the candidate ORF may not yield detectable activity because of the accumulation of one or more down mutations in its nucleic acid sequence. Even if such a mutation is identified, it may only be mutable if within the sequence encompassed by the PCR primers. If outside this region, ORF sequences are essentially immutable, and the gene product, if any, cannot be biochemically characterized with this approach.

In yet another preferred embodiment of the present invention, the original microorganism from which the DNA sequence has been obtained may be grown up, crude extracts prepared, and tested for restriction endonuclease activity in the usual way described above. In the event that restriction endonuclease activity is found, then it may be related to the gene coding for it in several ways. First, if methylase clones are active, then they may be tested directly to see if the DNA from the cloned plasmid is resistant to the action of the restriction endonuclease, suggesting that they have matching specificities and so form part of the same restriction-modification system. Alternatively, the endonuclease may be purified to homogeneity, some N-terminal or other protein sequence obtained, and the protein sequence compared with the predicted protein sequence from the original sequenced gene.

The following Examples are given to illustrate embodiments of the present invention, as it is presently preferred to practice. It will be understood that these Examples are illustrative, and that the invention described herein is not to be considered as restricted thereto except as indicated in the appended claims.

The references cited above and below are herein incorporated by reference.

EXAMPLE I

MjaI Restriction Endonuclease

The restriction endonuclease MjaI, from *Methanococcus jannaschii*, has previously been characterized biochemically and shown to recognize the sequence CTAG (Zerler, B., Myers, P. A., Escalante, H. and Roberts, R. J. cited in REBASE—see Roberts, R. J. and Macelis, D. *Nucl. Acids Res.* 26: 338–350 (1998)), but the gene had not been cloned. With the recent determination of the complete sequence of the *M. jannaschii* genome (Bult et al. *Science* 273: 1058–1073 (1996)) the sequence was searched using the BLAST program (Altschul, et al. *J. Mol. Biol.* 215: 403–410 (1990)) to identify candidate restriction enzyme and methylase genes. In brief, all open reading frames in the sequence were compared with the RM sequence database that contained the published sequences of all DNA methylases and restriction endonucleases that had been compiled from entries in GenBank. Each match against an entry in this database was recorded and the corresponding region of the *M. jannaschii* genome was examined to determine if the hit could be part of a restriction-modification system. Typically, most good hits were between a known DNA methylase gene and an open reading frame present in the *M. jannaschii* genome.

By using BLAST it was found that one open reading frame (MJ0985) showed great similarity to a known DNA methylase gene, encoding M.MthZI, a methylase which forms part of a restriction-modification system in *Methanobacterium thermoformicicum* that recognizes the sequence CTAG (Nolling, J. and deVos, W. M., *Nucl. Acids Res.* 20: 5047–5052, (1992); Nolling, J., Van Eeden, et al., *Nucl. Acids Res.* 20: 6501–6507 (1992)). The regions of similarity included the motifs characteristic of an N4C- or N6A-methylase (Wilson, G. G., *Meth. Enzymol.* 216:259–279 (1992), Timinskas et al. *Gene* 157:3–11 (1995)). Immediately adjacent to this *M. jannaschii* putative methylase gene was another open reading frame, MJ0984, that resembled the gene encoding the restriction enzyme MthZI. This open reading frame, which had never previously been investigated biochemically, was tested for its coding potential using the method disclosed in accordance with the present application. This Example documents the identification of an active restriction endonuclease from a previously unknown DNA sequence.

DNA from *M. jannaschii*, was a gift from G. Olson, University of Illinois, Urbana. The open reading frame, MJ0984, predicted to encode the MjaI restriction endonuclease comprised residues 4687–5355 of the GenBank entry U67541. Primers were selected with the following sequences:

5'-pGTTTAATACGACTCACTATAGGGTTAGGAGGTATTA(GAT
(A)TGGTGAAACTTATGAAAAAATTG-3' (SEQ ID NO:1)

Note that the marked (A) is a G in the original genome. It was changed to an A to ensure a better translational start. This is the start codon of the open reading frame. Sequences preceding the (A) are not present in the genome, but contain the T7 RNA polymerase promoter sequence and a good ribosome binding site.

5'-pGTTGGATCCGCAAAAAAGAATAGGAATGGATTTTAATCA-3'
(SEQ ID NO:2)

These primers were first used to prepare an amplified sample of the region of the *M. jannaschii* genome containing the MJ0984 open reading frame. The MJ0984 open reading frame was amplified from genomic *M. jannaschii* DNA in three PCR reactions (80 µl each) that contained 0.4 µM each of the four dNTPs, 0.02 µg *M. jannaschii* genomic DNA, 0.4 µM primer 1, 0.4 µM primer 2, 1.2 units Vent® DNA polymerase and either 3 mM, 4.5 mM or 6 mM MgSO₄ in 1×NEB ThermoPol buffer. The reaction was heated to 95° C. for three minutes, and then 5 cycles of amplification at 95° C. for 30 seconds, followed by 52° C. for 30 seconds, followed by 72° C. for 45 seconds were performed, followed by 20 cycles at 95° C. for 30 seconds, 62° C. for 30 seconds and 72° C. for 45 seconds. 10 µl of each PCR reaction was analyzed by gel electrophoresis, and a prominent band of the expected size was observed in the 4.5 mM and 6 mM MgSO₄ reactions. These two reactions were combined, extracted with phenol/chloroform, washed in an Amicon Microcon-100 microfiltration device by four serial 20-fold dilution and concentration steps into TE buffer and the final 40 µl of concentrated product was stored at 4° C.

The same primers, 1 and 2, were then used in a set of 24 PCR reactions (100 µl each) that contained 0.8 mM each of the four dNTPs, 0.01 µg pre-amplified *M. jannaschii* DNA described above, 0.5 µM primer 1, 0.5 µM primer 2, and 2 units Vent® DNA polymerase (New England Biolabs, Inc., Beverly, Mass.) in 1×NEB ThermoPol Buffer. The reaction mix was heated at 95° C. for three minutes, and then subjected to 25 rounds of PCR, incubating at 95° C. for 30 seconds, 46° C. for 30 seconds, 72° C. for 50 seconds. Finally the reaction was incubated at 30° C. for two minutes. The crude mixture from the PCR reactions was then combined and purified. First a standard phenol/chloroform extraction was carried out to remove protein and the DNA was precipitated with isopropanol and then spun at 9,000 rpm for 7 mins in the microfuge through Microcon 50 filters. The concentrated PCR product 300 µg/ml was collected at 2,000 rpm for 5 min. The product was checked on a 1% agarose gel.

The transcription and translation of the putative MjaI gene was performed using a rabbit reticulocyte Protein Truncation Kit (Boehringer Mannheim). The PCR product 0.4 µg (2 µl), transcription mix (2.5 µl) and 5.5 µl of RNase free water were incubated at 30° C. for 30 min. The translation mix (40 µl) was added and incubated at 30° C. for 1 hr. The transcription/translation mix was then tested for newly-formed restriction enzyme activity corresponding to the formation of MjaI.

Serial dilutions were performed by mixing 2 µl, 1 µl, 0.5 µl, 0.25 µl translation product per 20 µl final reaction volume in 1×NEB buffer 4 (50 mM potassium acetate, 20 mM Tris-acetate, 10 mM Magnesium acetate, 1 mM dithiothreitol, 100 µg/ml BSA) containing 25 µg/ml substrate DNA. The reactions were incubated at 37° C. overnight. The reactions were run on a 1.0% agarose gel. As a positive control Bfa I (20 units, New England Biolabs, Inc.), an isoschizomer of MjaI, was used to cut the substrate DNA under the same reaction conditions. As a negative control the DNA was incubated with the transcription/translation mix to which no template DNA (PCR product) had been added.

The agarose gel results showed that the test DNA was digested by the translation/transcription mix only when that mix had been primed with PCR product from the putative MjaI-encoding plasmid DNA. The banding pattern produced was identical to that produced by BfaI (FIG. 1, lanes 2 and 4). A double digest between MjaI and BfaI gave no additional bands (FIG. 1, lane 3). These results allow the identification of the open reading frame present in the starting plasmid as encoding MjaI restriction endonuclease.

EXAMPLE II

HhaI Restriction Endonuclease

The genes encoding the restriction endonuclease and methylase of the HhaI system have previously been cloned and sequenced (U.S. Pat. No. 4,999,293). Examination of the sequence showed a characteristic 5-methyl cytosine gene followed by an open reading frame on the complementary strand that was known to be the HhaI restriction endonuclease. This system was used as a test to show that it would be possible to make a sufficient quantity of the restriction enzyme in vitro to allow its detection using standard procedures.

First, plasmid DNA encoding the HhaI restriction system was prepared from *E. coli* NEB691 (New England Biolabs). The *E. Coli* cells containing the recombinant plasmid were incubated in 10 ml LB in a roller at 37° C. overnight. Cells were pelleted at 4,000 rpm for 30 sec at 4° C. and the supernatant was discarded. The pellet was resuspended in 1 ml 1×GTE (50 mM glucose, 25 mM Tris.HCl, 10 mM EDTA, pH 8.0) and lysed by adding 0.2 M NaOH, 1% SDS (2 ml). The precipitate was spun for 3 min at 15,000 rpm at 4° C. and the supernatant was transferred to a clean centrifuge tube. Isopropanol was added to the supernatant and it was incubated on ice for 10 min. The mixture was spun at 15,000 rpm for 5 min at 10° C. and the supernatant was discarded. The pellet was dried and resuspended in 100 μg/ml pancreatic RNase in 850 μl 1×TE (10 mM Tris.HCl, 1 mM EDTA, pH 8.0). The reaction was incubated at room temp. for 1 hour and spun at 14,000 rpm at 4° C. for 5 min. The supernatant was discarded and the pellet was resuspended in 100 μl 1×TE. The product was checked on a 1% agarose gel.

Primers were synthesized with the following sequences:

5'-pTAATACGACTCACTATAGGGAATAATTTTGTT TTAACTTTAA GAAGGAGAATGAAAATGAATTGGAAAG-3' (SEQ ID NO:3)

5'-pCAATTATAAAGAAATAGCTGCC-3' (SEQ ID NO:4)

These primers were used in a set of 24 PCR reactions (100 μl each) that contained 0.8 mM each of the four dNTPs, 0.1 μg plasmid DNA, 0.5 μM primer 3, 0.5 μM primer 4, and 2 units vent DNA polymerase in 1×NEB ThermoPol Buffer. The reaction mix was heated at 95° C. for three minutes, and then subjected to 25 rounds of PCR, incubating at 95° C. for 30 seconds, 46° C. for 30 seconds, 72° C. for 50 seconds. Finally the reaction was incubated at 30° C. for two minutes. The PCR reactions were then combined, phenol/chloroform extracted and the DNA was precipitated and resuspended in 1×TE at 300 μg/ml.

The transcription and translation of the HhaI gene PCR product was performed using a rabbit reticulocyte Protein Truncation Kit (Boehringer Mannheim). The PCR product 0.6 μg (2 μl), transcription mix (2.5 μl) and 5.5 μl of RNase free water were combined and incubated at 30° C. for 30 min. The translation mix (40 μl) was added and incubated at 30° C. for 1 hr. The transcription/translation mix was then tested for newly-formed restriction enzyme activity corresponding to the formation of HhaI.

Serial dilutions were performed by mixing 2 μl, 1 μl, 0.5 μl, and 0.25 μl transcription/translation product per 20 μl final reaction volume in 1×NEB buffer 4 containing 25 μg/μl substrate DNA. The reactions were incubated at 37° C. for one hour. The reactions were analyzed on a 1.0% agarose gel. As a positive control authentic Hha I (20 units, New England Biolabs, Inc.) was used to cut the substrate DNA under the same reaction conditions. As a negative control the DNA was incubated with the transcription/translation mix to which no template DNA (PCR product) had been added. The agarose gel results showed that the substrate DNA was digested by the translation/transcription mix only when that mix had been primed with the HhaI endonuclease PCR product. The banding pattern produced was identical to that produced by HhaI, thus demonstrating the utility of the in vitro transcription/translation system to product an active identifiable restriction endonuclease.

EXAMPLE III

A 2nd Putative New Restriction Endonuclease From *M. jannaschii* (ORF 1328—GTNNAC, MjaIV)

Another of the open reading frames that showed a good match to a known methylase gene was MJ1328. This gene is similar to the gene for M.HincII, which recognizes the sequence GTYRAC. The open reading frame immediately preceding MJ1328 shows some low similarity to the gene for the HincII restriction enzyme and so is a good candidate for a new restriction enzyme of the same or related specificity. This open reading frame, MJ1327, comprises residues 1748–2485 of GenBank entry U67573. However, because *M. jannaschii* is a thermophile that normally grows at high temperatures, this new putative restriction enzyme encoded by the open reading frame MJ1327 may be anticipated to work at much higher temperatures than Hincil, isolated from the mesophile *Haemophilus influenzae* serotype c (Landy et al. *Biochemistry* 13: 449–456, 1974).

The ORF designated MJ1328 by TIGR (The Institute for Genomic Research), which comprises residues 3148 to 4044 of GenBank entry U67573, contains only the 3' portion of the believed methylase gene, which complete methylase gene would be found from position 2472 to 4044 of GenBank sequence U67573, with a frameshift present between positions 3148 and 3305. The 5' portion of this ORF, that not contained in the TIGR designation, contains the methylase motifs (GxGxF and NPPY), while the whole has homology to M.HincII.

To characterize MJ1327, the ORF was PCR amplified from genomic *M. jannaschii* DNA using the following two oligonucleotides as primers: forward (coding strand) primer, having a BamHI cloning site, T7 promoter sequence, and NcoI cloning site:

5'-GTTGGATCCTMTACGACTCACTATAGGAACA GACCACCATGGTG GTAAAATTGGTTAATAAC-3' (SEQ ID NO:7)

reverse primer having a BamHI cloning site:

5'-GTTGGATCCGATTGTAGAAAGATTTATCATTA ATTC-3' (SEQ ID NO: 8)

The PCR reaction was performed by combining: 20 μl 10×NEB ThermoPol Buffer (NEB), 16 μl dNTP solution (4 mM), 15 μl forward primer (10 μM), 15 μl reverse primer (10 μM), 135 μl dH20, 1.5 μl *M. jannaschii* genomic DNA (100 ng) mixing, then adding:

4 μl Vent® exo-DNA polymerase, 1 μl Vent® DNA polymerase, dividing into 5 tubes of 40 μl each, adding 0.4, 0.8, 1.2, 1.6 μl 100 mM MgSO4 solution to one tube each to create reactions of 2, 3, 4, 5 and 6 mM Mg++ concentrations.

These five tubes were incubated at 95° C.–2 min for one cycle, 95° C.–30 sec, 52° C.–30 sec, 72° C.–1 min 15 sec for 5 cycles, then 95° C.–30 sec, 58° C.–30 sec, 72° C.–1 min 15 sec for 27 cycles.

Product was observed in the 4 and 5 mM Mg++ reactions. The product obtained was used as template and 15 more cycles of amplification in a 500 μl reaction as above was performed to obtain a larger quantity of PCR product. The amplified DNA was phenol/chloroform extracted and alcohol precipitated, then cleaved with BamHl, phenol-chloroform extracted, alcohol precipitated, resuspended in TE and ligated to pUC19 DNA previously cleaved with BamHl and dephosphorylated. The ligated product was transformed into *E. coli* ER2170 cells by electroporation, and the transformed cells were grown in LB broth+100 μg/ml ampicillin overnight. A sample of these transformed cells, *E. coli* ER2170-pUC-MjaIV, was deposited under the terms and conditions of the Budapest Treaty with the American Type Culture Collection on Sep. 1, 1998 and received ATCC Accession No. 98860.

The cells were then harvested by centrifugation, resuspended in sonication buffer (20 mM Tris, 1 mM DTT, 0.1 mM EDTA, pH 7.5), lysed by sonication and the extract was clarified by centrifugation. This crude extract was assayed for restriction activity using λ DNA in NEBuffer 4. Specific cleavage of λ was observed and the restriction activity was purified by passing the crude extract through a heparin-sepharose column and step eluting the column with 0.5M and 1M NaCl in sonication buffer. The purified restriction activity was mapped on pBR322, φX174 and M13mp18 DNAs, and the cleavage pattern was found to be consistent with cleavage at the sequence 5'-GTNNAC-3'. This new endonuclease was named MjaIV. The cleavage position within the recognition sequence was determined by the primer extension method using M13mpl8 and primer NEB #1224 and found to be 5'-GTN↓NAC-3', cleaving between the 2 N residues to produce blunt ends.

The HincII sequence, 5'-GTYRAC-3', originally postulated for this restriction system, is a subset of the actual recognition sequence of MjaIV, thus explaining the homology noted previously between MJ1328 and the gene for M.HincII and MJ1327 and the gene for HincII.R.

MjaIV methylase (ORF MJ1328 plus 5' end) will be put into an appropriate vector and expressed in *E. coli* to protect the *E. coli* host DNA from degradation by the MjaIV endonuclease, which will be cloned into a strongly expressing, regulated vector, such as pET21 (T7) or pRRS. The MjaIV endonuclease may then be produced by culturing the host carrying the gene for MjaIV, inducing with appropriate conditions, harvesting the cells and purifying the MjaIV endonuclease by a combination of standard protein purification techniques.

EXAMPLE IV

A 3rd Putative New Restriction Endonuclease From *M. jannaschii* (ORF 1449—GGNCC, MjaII)

Another of the open reading frames that showed a good match to a known methylase gene was MJ1448. This gene is quite similar to the gene for M.MvaI, which recognizes the sequence CCWGG. At the time of the original analysis, the open reading frames on both sides of MJ1448 had no matches either to known restriction enzyme genes or to any other open reading frames present in GenBank. One of these was likely to be a restriction enzyme gene, and so both were tested using the methods of Example I.

To test which of these open reading frames was the putative new restriction enzyme, a detailed protocol similar to that of Example I was employed. The segment of the genome of *M. jannaschii* containing the open reading frame MJ1447 comprising residues 8643–9788 of GenBank entry U67585 was amplified using the following PCR primers:

5'-GTTTAATACGACTCACTATAGGGTTAGGAGGT ATTACAT(A)TG ATAAAATTTGGAGAAGCAGTTTTG-3' (SEQ ID NO:9)

Note that the marked (A) is the start codon of the open reading frame. Sequences preceding the (A) are not present in the genome, but contain the T7 RNA polymerase promoter sequence and a good ribosome binding site.

5'-GTTGGATCCGTGTAAAGTTTTTTTGCTGGCTG-3' (SEQ ID NO:10)

The product of this open reading frame were tested in a manner similar to that of Example I and was found not to be enzymatically active at cleaving DNA.

The candidate ORF MJ1449 was identified as outlined above. The segment of the genome of *M. jannaschii*, comprising residues complementary to 11380–12492 in GenBank entry U67585, was amplified by PCR using the following two oligonucleotides as primers:

5'-CCTCCTCTAGAAGAAGGAGATATACCATGCCA CTAAGTAAAA ATGTTATAG-3' (SEQ ID NO:11)

5'-GGAGGGATCCTCGAGCGCTTGACTGMTAGTT ATTTTTGCAT ATATTTATTGTATAATTC-3' (SEQ ID NO:12)

Using the protocol described in Examples IX and X below, ORF MJ1449 was stably cloned in DH5αF' and the construction designated pLT7-M1449. When transformed into ER2566P (where "P" indicates the presence of pLysP), the protein expressed from this construct exhibited an activity consistent with that of a restriction endonuclease cleaving the sequence GGNCC, at an assay temperature of 65° C. A sample of these transformed cells, *E. coli* ER2566P pLT7-M1449, was deposited under the terms and conditions of the Budapest Treaty with the American Type Culture Collection on Sep. 1, 1998 and received ATCC Accession No. 202168.

This activity was previously detected biochemically from crude lysates of *M. jannaschii*, and designated R. MjaII, but the gene was unknown. Induction of pLT7-M1449 at 37° C. was lethal, indicating that the protein is also active at this temperature.

EXAMPLE V

Expression of R.SfiI in a Coupled Transcription/translation System from *E. coli*

The restriction endonuclease SfiI from *Streptomyces fimbriatus*, recognizing the octanucleotide sequence 5'-GGCCNNNN↓NGGCC-3', (SEQ ID NO:13) has been cloned and overexpressed in *E. coli* (U.S. Pat. No. 5,616, 484). The overexpression construct (Sfi4-2) consists of the SfiI DNA methyltransferase expressed on the vector pACYC184, under control of its own promoter, and the SfiI endonuclease expressed on a pUC19 derivative containing a T7 promoter, such that the gene is under control of either the Plac promoter or the T7 promoter. Plasmid DNA was purified from a 4 liter culture of *E. coil* ER1451 (Elisabeth Raleigh, New England Biolabs, Inc., Beverly, Mass.) harboring both plasmids using the alkaline lysis method followed by isopycnic banding in two successive cesium chloride gradients to remove all traces of contaminating chromosomal DNA.

An S-30 extract was prepared from a 10-liter culture of *E. coli* strain D-10 (ma-10, relA1, spoT11, metB1; Gesteland, R. F., *J. Mol. Biol.* 16:67 (1966)), an RNase I-deficient K-12 derivative, as described (Ellman, et al., *Methods Enzymol.* 202:301–336 (1991)).

In vitro protein synthesis reactions (30 μl final volume) contained the following: 56.4 mM Tris-acetate, pH 7.4; 1.76 mM dithiothreitol; 36 mM ammonium acetate; 72 mM potassium acetate; 9.7 mM calcium acetate; 6.7 mM magnesium acetate; 1.22 mM ATP (Na), 0.85 mM each of GTP (Na), CTP (Na), and UTP (Na); 27 mM potassium phosphoenol pyruvate; 0.35 mM each of the 20 amino acids; 19 mg/ml polyethylene glycol 8000; 35 mg/ml folinic acid; 27 mg/ml pyridoxine-HCl; 27 mg/ml NADP; 27 mg/ml FAD; 11 mg/ml p-aminobenzoic acid; 170 mg/ml *E. coli* tRNA; 100 μg/ml Sfi4-2 plasmid DNA; 25000 U/ml T7 RNA polymerase (where indicated) and 8.5 μl S-30 extract. Reactions were incubated at 37° C. for 1 hour on a rotary shaker (200 rpm), cooled to 0° C., and centrifuged 1 minute to pellet precipitated proteins.

The reaction supernatants were then assayed for SfiI activity in 25 μl reactions containing 1 μg Adenovirus-2 genomic DNA (35,937 bp) in NEBuffer 2 (10 mM Tris-HCl, pH 7.9, 50 mM NaCl, 10 mM MgCl2, 1 mM DTT), 100 μg/ml BSA, and three-fold serial dilutions (in NEBuffer 2) of the in vitro reaction supernatant. Reactions were incubated at 50° C. for 60 minutes and analyzed by agarose gel electrophoresis. As these reactions did not contain S-adenosylmethionine, a necessary cofactor for the SfiI DNA methyltransferase (MTase), any MTase synthesized in the translation reaction from the Sfi4-2 DNA template would not be active during the endonuclease assay reaction.

Figure 2:
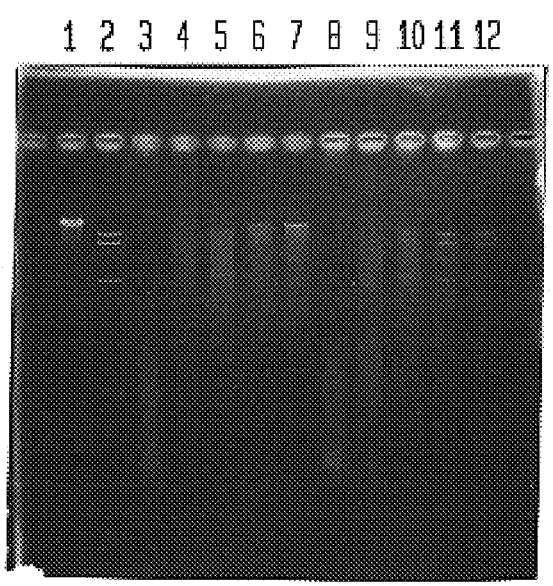
FIG. 2 is the agarose gel electrophoresis of R.SfiI activity in coupled transcription/translation reactions. SfiI digests of Adenovirus-2 DNA (35,927 bp) were carried out as described in the text. Lane 1: Uncut DNA. Lane 2: DNA digested with 10 units purified SM (NEB). Lanes 3–7: DNA digested with serially diluted reaction supernatant of in vitro transcription/translation reaction without added T7 RNA polymerase. Lanes 8–12: DNA digested with serially diluted reaction supernatant of in vitro transcription/translation reaction with added T7 RNA polymerase. Lanes 3 & 8: 3 µl reaction supernatant. Lanes 4 & 9: 1 µl reaction supernatant. Lanes 5 & 10: 0.3 µl reaction supernatant. Lanes 6 & 11: 0.1 µl reaction supernatant. Lanes 7 & 12: 0.03 µl reaction supernatant. The expected sizes of products from a complete SfiI digestion are 16,284, 12,891, 5,739 and 1,023 bp.

The results (FIG. 2) demonstrate complete cleavage of Adenovirus-2 substrate DNA at the highest dilution tested (lane 12) for the T7 polymerase-directed translation reaction (0.03 µl of reaction supernatant), corresponding to a yield of synthesized SfiI activity of at least 33000 units per ml of in vitro translation reaction. Assuming a specific activity of 20,000 units/mg and a monomer molecular mass of 25 kDa, this corresponds to roughly 1,000 synthesized R.SfiI molecules per molecule of input DNA template. For the reaction without added T7 RNA polymerase, in which transcription was presumably from the weaker E. Coli $P_{lac}$ promoter, the yield of SfiI activity was roughly 10-fold lower (cf. lanes 5 and 12), or 3000 units per ml, indicating that protein synthesis is transcription limited in this system.

EXAMPLE VI

A new MboI Isoschizomer from M. jannaschii (ORF 600—GATC, MjaIII)

The MJ600 ORF, comprising residues 5632 to 6504 of GenBank entry U67508, was predicted to encode an isoschizomer of MboI on the basis of homology to MboI and LlaII, as determined by the method of Example I.

MJ600 was amplified and cloned in the same manner as MJ1327, by the method of Example III, using as primers:
(forward)
  5'-GTTGGATCCTMTACGACTCACTATAGGMCAG ACCACCATG AATTTTGAATACATCATTAACAG-3' (SEQ ID NO: 13)
(reverse)
  5'-GTTGGATCCAAATTGAATAATGGTATCATTCAC-3' (SEQ ID NO: 14)
and the restriction activity was found to cleave at 5'-GATC-3'. This confirms that this ORF encodes an isoschizomer of MboI, as predicted. This isoschizomer, MjaIII, from the thermostable organism M. jannaschii, can be expected to be significantly more thermostable than MboI.

EXAMPLE VII

Expression of HindIII in a Coupled Transcription/translation System From E. coli The genes encoding the restriction endonuclease and methylase of the HindIII system have previously been cloned and sequenced (U.S. Pat. No. 5,180,673). The present invention's competence in identifying restriction endonucleases was further demonstrated by the use of the following standard procedures to make sufficient quantity of HindIII enzyme in vitro to allow its detection.

First, plasmid DNA encoding the HindIII restriction system was prepared from E. coli NEB 325 (New England Biolabs) by standard methods.

Primers were synthesized with the following sequences:
  5'-CGAAATTAATACGACTCACTATAGGGAGACCA CAACGGTTAA GGAGGTGACAAAAIGM-GAAAAGTGCGTTAGAG-3' (SEQ ID NO:15)
  5'-AAATGGATCCAGAATTATAAATACAGTCTATCA TTAC-3' (SEQ ID NO:16)

These primers were used in a set of 5 PCR reactions (100 µl each) that contained 0.2 mM each of the four dNTPs, 0.1 µg plasmid DNA, 0.5 µM of each above mentioned primer, and 2 units Vent® DNA polymerase in 1×NEB ThermoPol Buffer (10 mM KCl, 20 mM Tris-HCl (pH 8.8 at 25° C.), 10 mM $(NH_4)_2SO_4$, 4 mM $MgSO_4$, 0.1% Triton X-100). The reaction mix was heated at 95° C. for 30 seconds, 55° C. for 45 seconds, 72° C. for 75 seconds for 20 cycles. Finally, the reaction was incubated at 72° C. for 10 minutes. The reactions were combined and phenol/chloroform extracted. The DNA was concentrated and primer dimer products partially removed by using a Microcon 50 device according to the manufacturers instructions for 3 rounds of 20-fold concentration and dilution. The purified PCR product was concentrated to 50 µg/ml.

The transcription and translation of the HindIII gene was performed using a rabbit reticulocyte Protein Truncation Test Kit (Boehringer Mannheim). The PCR product (0.4 µg (2 µl)), transcription mix (2.5 µl) and RNase free water (5.5 µl) were combined and incubated at 30° C. for 30 min. The translation mix (40 µl) was added and incubated at 30° C. for 1 hr. The transcription/translation reaction was then tested for newly formed HindIII restriction enzyme activity.

Serial dilutions of the transcription/translation reaction were performed in NEB buffer 2 (50 mM NaCl, 10 mM Tris-acetate, 10 mM $MgCl_2$, 1 mM dithiothreitol, 100 µg/ml BSA) containing 25 µg/ml λ phage substrate DNA using 1.6 µl, 0.53 µl, 0.17 µl or 0.06 µl transcription/translation reaction product per 20 µl final reaction volume in 1×NEB buffer 2 containing λ DNA. The reactions were incubated at 37° C. for 14 hours. As a positive control, authentic HincIII (20 units, New England Biolabs, Inc.) was used to cut the substrate DNA under the same reaction conditions. As a negative control, the DNA was incubated with the transcription/translation mix to which no template DNA (PCR product) had been added.

HindIII restriction activity was clearly observed in the in vitro transcription/translation reaction, demonstrating the efficacy of the in vitro method described in the instant application.

EXAMPLE VIII

In Vitro Transcription/Translation of PacI Restriction Endonuclease

The gene encoding the PacI restriction endonuclease has previously been cloned and sequenced (Richard D. Morgan, New England Biolabs, Inc., unpublished observations). It has been observed that clones of PacI are unstable in E. coli, presumably due to the lack of a PacI methylase on these clones. The present invention's competence in identifying restriction endonucleases was further demonstrated by the use of the following standard procedures to make sufficient quantity of PacI enzyme in vitro to allow its detection and identification.

First, Pseudomonas alcaligenes genomic DNA was obtained from NEB 585 (New England Biolabs, Inc., Beverly, Mass.). See also U.S. Pat. No. 5,098,839.

Primers were synthesized with the following sequences:
  5'-GTTGGATCCTAATACGACTCACTATAGGAACA GACCACCATG ACGCAATGTCCMGGTG-3' (SEQ ID NO:17)
  5'-GTTGGATCCGTCGACTTGGCAAAGCCCTCTTC-3' (SEQ ID NO:18)

These primers were used in a set of 8 PCR reactions (100 µl each) that contained 0.2 mM each of the four dNTPs, 0.1 µg genomic DNA, 0.5 µM of each above mentioned primer, and 2 units Vent® DNA polymerase in 1×NEB ThermoPol Buffer (10 mM KCl, 20 mM Tris-HCl (pH 8.8 at 25° C.), 10 mM $(NH_4)_2SO_4$, 4 mM $MgSO_4$, 0.1% Triton X-100). The reaction mix was heated at 95° C. for 30 seconds, 57° C. for 30 seconds, 72° C. for 65 seconds for 27 cycles. The PCR reactions were combined and a standard phenol/chloroform extraction was carried out to remove protein. The DNA was concentrated and primer dimer products partially removed using an Amicon Microcon-50 device as in Example VII.

The transcription of the PacI gene was performed using a rabbit reticulocyte Protein Truncation Test Kit (Boehringer Mannheim). The PCR product 0.4 μg (2 μl), transcription mix (2.5 μl) and 5.5 μl of RNase free water were combined and incubated at 30° C. for 45 min. Transcription mix (8 μl) containing m7G(5')ppp(5')G 5' capped mRNA was added to 42 μl of Ambion T/T Wheat Germ translation mix (11 μl RNase free water, 2.5 μl 1 M KOAc, 3.5 μl Amino Acid Mix, 25 μl Translation extract) and incubated at 27° C. for 1 hr. The transcription/translation reaction was then tested for newly formed PacI restriction enzyme activity.

Substrate DNA was digested by the transcription/translation mix only when that mix had been primed with PCR product from the *Pseudomonas alcaligenes* genomic DNA. The lanes with primed transcription/translation product produced banding patterns identical to the lanes with authentic PacI, again demonstrating the efficacy of the method described in the instant Application.

EXAMPLE IX

Stable Cloning of PacI Restriction Endonuclease

The restriction endonuclease PacI has been previously characterized biochemically and shown to recognize the sequence TTAATTAA. Despite repeated attempts, the gene has not been usefully cloned due to the apparent lack of a cognate methylase, and the inherent lethality of the gene product. The gene encoding PacI was used as a test to show that it would be possible to: 1) establish a stable clone of a gene encoding a lethal protein, and 2) show that the expression of such a cloned gene could be electively modulated using standard laboratory techniques.

Genomic DNA from *Pseudomonas alcaligenes* (NEB 585) was prepared by standard methods.

Primers were synthesized with the following sequences:
5'-CCTCCTCTAGAAGAAGGAGATATACCATGACG CAATGTCCAA GGTGCC-3' (SEQ ID NO:19)
5'-GGAGGGATCCTCGAGCGCTTGACTGMTAGTT AGG-3' (SEQ ID NO:20)

Approximately 0.5 μg of the *P. alcaligenes* DNA was used as template in a 100 μl PCR reaction containing 0.2 mM each of the four dNTPs, 100 pmol of each primer, 4 units of Vent® DNA polymerase (VDpol) in 1×NEB ThermoPol Buffer. The reaction mix was heated to 94° C. for 2 minutes, and then subjected to 25 cycles of PCR, incubating at 94° C. for 1 minute, 58° C. for 30 seconds, and 72° C. for 30 seconds. Finally the reaction was held at 72° C. for five minutes. 10% of the reaction product was checked on a 1% agarose gel, and the balance stored at −20° C. until further use. The reaction was subjected to standard phenol/chloroform/isoamyl alcohol, then chloroform extractions to partition the protein and the PacI amplicon (DNA product of the PCR reaction). The amplicon was precipitated from the aqueous fraction by supplementing it with sodium acetate (pH 5.2) to 0.3 M, addition of 2.5 volumes of absolute ethanol, and storage at −20° C. overnight. The amplicon was recovered by centrifugation at 14,000 rpm at 4° C. for 20 minutes, at which point the supernatant was discarded. After allowing the DNA pellet to dry, it was redissolved in 50 μl of 10 mM Tris-HCl, pH 7.4.

Approximately 2 μg of the amplicon was incubated for 2 hours at 37° C. in a 50 μl restriction endonuclease reaction containing 1.0 mg/ml bovine serum albumin (BSA), 40 units each of XbaI and XhoI, in 1×NEB buffer #2. 50 μl of 10 mM Tris-HCl, pH 7.4 was added to the reaction to make the volume 100 μl. The reaction was subjected to phenol/chloroform and ethanol precipitation as described above. The pellet was dissolved in 25 μl of 10 mM Tris-HCl, pH 7.4. The resulting DNA preparation was electrophoresed on a 1% agarose gel, the desired band excised, and eluted from the agarose matrix. Approximately 0.5 μg of pLT7K was prepared in a similar manner. The eluates were mixed, then subjected to phenol/chloroform and ethanol precipitation as described above. The dry DNA mixture was dissolved in 20 μl 1×NEB ligase buffer and incubated with 800 units of T4 DNA ligase at 16° C. overnight.

The ligation was subjected to phenol/chloroform and ethanol precipitation as described above, and dissolved in 30 μl of 10 mM Tris-HCl, pH 7.4. 10 μl of this preparation was added to 85 μl of electrocompetent *E. coli* strain DH5αF' (LTI) on ice. Electroporation was done in a 0.1 cm cuvette chamber using a BioRad Genepulser (model #1652102) set at 1.88 kvolts. The contents of the cuvette were removed into a 1.5 ml tube containing 0.5 ml Luria broth supplemented to 20 mM glucose (LB-glc) that had been prewarmed to 42° C. The tube was placed into a 40° C. shaker for approximately 45 minutes, at which point it was removed to a 42° C. heat block. Three fractions of the preparation (2%, 20%, and 78%) were spread onto LB-glc agar plates (prewarmed to 40° C.) containing 100 μg/ml ampicillin (LB-glc-Ap). Plates were incubated at 40° C. overnight.

The following day, ten transformant colonies were randomly picked and dispersed into 5 ml of prewarmed LB-glc-Ap media. These cultures were incubated overnight in a 40° C. shaker, at which point plasmid DNA was isolated by standard procedures. Plasmid DNAs were screened by restriction digest. 7 out of the 10 selected clones had the desired construction:

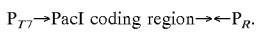

$P_{T7}$→PacI coding region→←$P_R$.

Putative positives were subjected to single-pass sequencing reactions of the 5'-end of the insert. Five of the seven displayed no deviation from the expected sequence, and a representative clone, designated pLT7-Pac.3, was selected for further characterization.

pLT7-Pac.3 was transformed into *E. coli* strain ER2566P using a variation of a standard chemical method. Approximately 0.05 μg of plasmid DNA was incubated with 100 μl of cells for 30 minutes on ice. The mixture was warmed to 42° C. for two minutes, at which point 0.9 ml of LB-glc was added that had been prewarmed to 42° C. The tube was placed into a 40° C. shaker for approximately 30 minutes, at which point it was removed to a 42° C. heat block. Two fractions of the preparation (2% and 20%) were spread onto LB-glc agar plates (prewarmed to 40° C.) containing 100 μg/ml ampicillin (LB-glc-Ap). Plates were incubated at 40° C. overnight. The following morning, three transformant colonies were randomly picked and dispersed into 5 ml of prewarmed LB-glc-Ap media. The cultures were incubated for approximately 4 hours in a 40° C. shaker, at which point 2.5 ml of each was added to 500 ml of prewarmed LB-glc-Ap media, and incubated in a 40° C. shaker until the culture had attained an O.D. $_{600nm}$ of approximately 0.7. IPTG was added to a final concentration of ~0.8 mM, the shaker temperature was adjusted to 30° C., and the culture incubated for an additional 4 hours. Approximately 1 g of cells was recovered by centrifugation (6000 rpm, 4° C., 15 minutes) and stored at −70° C. overnight.

The cell pellet was suspended (on ice) in 20 ml of a buffer (PacI core buffer) consisting of: 20 mM KPO4, pH 6.0; 50 mN NaCl; 10 mM B-mercaptoethanol; 0.1 mM EDTA; 5% glycerol. Cells were lysed by the addition of Triton X-100 to 0.1%, lysozyme to 1 µg/ml and, after warming briefly to 20° C., alternating sonication/cooling on ice. The preparation was clarified by centrifugation (10,000 rpm, 20 minutes, 4° C.), and the supernatant removed to a fresh tube on ice.

The cleared lysate was applied to a heparin-sepharose column that had been previously equilibrated with PacI core buffer. This was followed by an 8 column-volume wash. The flow-through and the wash fractions were collected and maintained on ice, as well as a small amount of the cleared lysate. The column was developed with a 50 ml gradient from 0.05–1.0 M NaCl. 1.0 ml fractions were collected and maintained on ice.

A low level of endonuclease activity consistent with that of PacI was detected in fractions distributed across the elution gradient. This indicated that the protein had bound poorly to the column and suggested that the protocol employed here, which had been optimized for *P. alcaligenes* lysates, was not optimal for *E. coli* lysates. Accordingly, the crude lysate and column flow-through were assayed for PacI activity, where it was clearly evident.

To test whether pLT7-Pac.3 would be stable and electively inducible in a production-scale expression system, a 20 liter culture was grown under conditions similar to those outlined above. A fresh transformation of pLT7-Pac.3 into ER2566P was done as outlined above. A colony was randomly selected, dispersed into 1 liter of media, and incubated in a 40° C. shaker overnight. This was used to inoculate a 20 liter fermenter run.

At an $OD_{600}$ of ~1.0, IPTG was added to a final concentration of 0.3 mM, the temperature reduced to 30° C., and incubation continued for an additional 4 hours. 38 grams of cells were harvested by continuous flow centrifugation and stored at –70° C. for 19 days. A sample of these transformed cells, ER2566P-pLT7-Pac.3, was deposited under the terms and conditions of the Budapest Treaty with the American Type Culture Collection on Sep. 1, 1998 and received ATCC Accession No. 202169.

A clarified extract was prepared and partitioned over a heparin-sepharose column with a 0.05–1.0 M NaCl gradient. This procedure yielded >800 units of PacI endonuclease/g of wet cells.

EXAMPLE X

Stable Cloning of NlaIII Restriction Endonuclease

Example IX illustrates that pLT7K enabled the establishment of a stable clone encoding PacI endonuclease, and that expression of this protein could be electively modulated. The octanucleotide recognition sequence for PacI does not occur in pLT7K. It is possible that the plasmid would be less stable if it were used to clone a gene encoding a restriction endonuclease capable of cleaving at one or more sites within the construct. Therefore, the reliability of pLT7K was subjected to a high stringency test by cloning the gene encoding restriction endonuclease NlaIII (R.NlaIII), absent the use of the NIaIII cognate methyltransferase (M.NlaIII).

R.NlaIII has been previously characterized biochemically and shown to recognize the sequence CATG (U.S. Pat. No. 5,278,060).

The NlaII restriction-modification system has also been previously cloned and sequenced, and the genes encoding M.- and R.NlaIII (nlaIIIM and nlaIIIR, respectively) identified (U.S. Pat. No. 5,278,060). In vivo, plasmid-borne alleles of nlaIIIR exhibit instability, even when M.NlaIII is expressed from a co-resident plasmid. In the absence of the cognate methylase, an nlaIIIR clone cannot be established using standard methods.

Using standard methods, plasmid DNA was prepared from cells that produce both M.- and R.NlaIII from separate plasmids.

Primers were synthesized with the following sequences:

5'-CCTCCTCTAGAAGAAGGAGATATACCATGAA AATCACAAAAA CAGAACT-3' (SEQ ID NO: 21)

5'-GGAGGGATCCTCGAGCGCTTGACTGAATAGT CATCCGTTATCTTC TTCATATAATTTC-3' (SEQ ID NO: 22)

These primers were used to generate an nIaIIIR amplicon containing sequences suitable for expression and directional cloning into pLT7K. Using the protocol described above, a gene encoding R. NlaII was cloned into the pLT7 vector, with 87% (13/15) recovery of the desired construct (designated pLT7-NlaIII). The clone could be established and stably maintained in both DH5aF' and ER2566P.

Addition of IPTG (to 1.0 mM) to 5 ml cultures of ER2566P-pLT7-NlaIII resulted in rapid cessation of cell growth, as compared to controls. One hour after IPTG addition, crude lysates were prepared using standard methods. When assayed, an endonuclease activity consistent with that of R.NlaIII was apparent.

Thus, pLT7K can be used to clone, maintain, and electively express genes whose products are capable of destroying the construct itself.

EXAMPLE XI

MjaV, A new Restriction Endonuclease From *M. jannaschii* Which Recognizes 5'-GTAC-3'

The open reading frame MJ1498, which comprises residues 9251 to 10129 of GenBank entry U67590, was identified as a likely methylase gene candidate, by virtue of its having amino acid sequences characteristic of amino methyltransferases; VTSPPY (SEQ ID NO: 24) and VLDPFM-GIGST (SEQ ID NO:25). The flanking ORFs, MJ1497 and MJ1499, were considered as possible endonuclease genes. A match in the database for ORF MJ1497 made this ORF seem a less likely candidate, but both MJ1497 and MJ1499 were PCR amplified from genomic *M. jannaschii* DNA and cloned into the T7 expression vector pAII17 in *E. coli*. Neither MJ1497 nor MJ1499 showed any restriction activity in the pools of clones prepared. The MJ1498 putative methylase gene was PCR amplified from genomic *M. jannaschii* DNA using the following two oligonucleotides as primers: forward (coding strand) BamHI cloning site, (NdeI cloning site):

5'-GTTGGATCCGTAATTAAGGAGGTAATTCATAT GGAGATAAAT AAAATCTAC-3' (SEQ ID NO:26)

reverse: SalI (EcoRI) cloning site:

5'-GTTGAATCCGTCGACTATTTAAATAAATGCATC-3' (SEQ ID NO: 27)

The PCR reaction was performed by combining:

20 ul 10× ThermoPol Buffer (New England Biolabs, Inc.)

16 ul dNTP solution (4 mM)

15 ul forward primer above (10 uM)

15 ul reverse primer above (10 uM)

133 ul $dH_2O$ 1.5 ul *M. jannaschii* genomic DNA 4 ul Vent® exo-DNA polymerase 1 ul Vent® DNA polymerase This master reaction mix was divided into 5 tubes of 40 ul each, to which were added 0.0, 0.4, 0.8, 1.2 and 1.6 ul of 100 mM MgSO$_4$ solution per tube to create reactions of 2, 3, 4, 5 and 6 mM Mg++ concentrations. These five tubes were incubated 95° C.–2 min for one cycle, 95° C.–30 sec, 48° C.–30 sec, 72° C.–1 min for 5 cycles, then 95° C.–30 sec, 58° C.–30 sec, 72° C.–1 min for 25 additional cycles. The amplified DNA was phenol/chloroform extracted, alcohol precipitated and resuspended in TE buffer. A portion of the amplified DNA was then cleaved with BamHI and SalI, phenol-chloroform extracted, alcohol precipitated and resuspended in TE. The cleaved DNA was then ligated to vector pSYX20 DNA previously cleaved with BamHI and SalI and gel purified. The ligated product was transformed into E. coli ER2566 cells and the transformed cells were grown overnight on LB plates containing 50 ug/ml kanamycin. Individual transformants were examined and minipreps of several clones containing the desired size insert were prepared. The cloned DNA was digested with various restriction enzymes in an attempt to find an enzyme which would cleave the pSYX20 vector but be unable to cut the MJ1498 clone, thus demonstrating that the cloned MJ1498 ORF was functioning as a methyltransferase to protect the vector DNA containing the MJ1498 gene against cleavage by that particular restriction endonuclease. It was found that the clones of MJ1498 were not cleaved by the restriction endonuclease RsaI, indicating that the methylase was protecting the GTAC sequence recognized by RsaI against cleavage. This showed that MJ1498 was able to function as a methyltransferase, as predicted, in E. coli. The methyltransferase activity could be methylating at GTAC, or GTAC could be a subset of the methyltransferase target sequence. To look for a cognate restriction activity, it was observed that the orf once removed from MJ1498, MJ1500, did not significantly match anything in the database by BLAST search. The possibility that an endonuclease might be one ORF removed from its cognate methylase was strengthened by the observation that MJ598 is the methylase and MJ600 is the endonuclease in the MjaIII system described above. The MJ1500 ORF, which comprises residues 767 to 74 of GenBank sequence U67591, was amplified from genomic M. jannaschii DNA using the following two oligonucleotides as primers:

forward (coding strand) BamHI cloning site, T7 promotor, kozak sequence:

5'-GTTGGATCCTAATACGACTCACTATAGGMCAG ACCACCATG GATGATAAGAGCTACTATG-3' (SEQ ID NO:28)

reverse:

5'-CATTAATATATAAATAAATACATAAAT-3' (SEQ ID NO: 29)

The PCR reaction was performed by combining:

20 ul 10× PCR BUFFER II (PE)

12 ul dNTP solution (4 mM)

15 ul forward primer above (10 uM)

15 ul reverse primer above (10 uM)

1.5 ul M. jannaschii genomic DNA 16 ul MgCl$_2$ (25 mM stock) (PE)

122 ul dH$_2$O 2 ul (10 u) AmpliTaq DNA polymerase (PE)

This master reaction mix was divided into 2 tubes of 100 ul each, to which were added 0.0 and 8 ul of 25mM MgCl$_2$ solution per tube to create reactions of 2 and 4 mM Mg++ concentrations.

These tubes were incubated at 95° C. for 2 min for one cycle, then 95° C.–30 sec, 40° C.–30 sec, 72° C.–1 min for 5 cycles, followed by 95° C.–30 sec, 48° C.–30 sec, 72° C.–1 min for 25 additional cycles. The amplified DNA was phenol/chloroform extracted, alcohol precipitated and resuspended in TE buffer at a concentration of 200 ug/ml. The amplified MJ1500 ORF was used for in vitro transcription/translation reactions as described above in Example I. The in vitro transcription/translation product was found to cut DNA at the sequence GTAC, demonstrating that MJ1500 is the cognate endonuclease to the MJ1498 methylase, and that this restriction system recognizes the sequence 5'-GTAC-3'.

EXAMPLE XII

A Putative New Restriction Endonuclease From M. jannaschii (ORF 1200/1199—not yet Identified)

During the search of the M. jannaschii genome sequence, as outlined in Example I, several open reading frames were identified that appeared to encode DNA methylase genes and were candidates to be part of Type II restriction-modification systems. One of these was the open reading frame labelled MJ1200, which showed the closest match to the known gene encoding the methylase M.Ddel. From the characteristic motifs (Posfai, et al., Nucl. Acids Res. 17:2421–2435 (1989)); Lauster, et al. J. Mol. Biol. 206:305–312 (1989)) present in this gene it is predicted to encode a cytosine-5 DNA methylase. However, because the variable region of this putative gene is not a good match for anything in the database it is possible that it recognizes a new DNA sequence. Immediately following this gene is an open reading frame that shows a good match to a ribosomal protein (L24E), while preceding the gene is an open reading frame (MJ1199) with no clear similarity to any other open reading frame present in GenBank. This open reading frame, MJ1199, is predicted to encode a new restriction enzyme and comprises the complementary strand residues 9158–10258 of the GenBank entry U67561.

To characterize the putative new restriction enzyme encoded by MJ1199, a detailed protocol similar to that of Example I will be employed. The segment of the genome of M. jannaschii containing the open reading frame MJ1199 will be amplified by PCR using as primers the following two oligonucleotides:

5'-GTTTAATACGACTCACTATAGGGTTAGGAGGT ATTACAT (A)TGAGAAAAATGTTTATTTGTTTGC-3' (SEQ ID NO:5)

Note that the marked (A) is a G in the original genome. It is changed to an A to ensure a better translational start. This is the start codon of the open reading frame. Sequences preceding the (A) are not present in the genome, but contain the T7 RNA polymerase promoter sequence and a good ribosome binding site;

5'-GTTGGATCCGGAGATTCCTGAGGCATCTTTG-3' (SEQ ID NO:6)

The PCR-amplified segment will be subjected to in vitro transcription/translation as detailed in Example I and the product will be tested for restriction enzyme activity by incubating the transcription/translation mix with various DNAs such as those of bacteriophages λ and T7 and Adenovirus-2. Incubations will be at various temperatures, ranging from 30° C. to 90° C. and for various lengths of time. After incubation the reactions will be examined by agarose gel electrophoresis to see if banding patterns, characteristic of restriction enzyme digestion, are present. If they are, then the new restriction enzyme will be characterized as to its recognition sequence and cleavage site in the usual way (Schildkraut, I. S., "Screening for and Characterizing Restriction Endonucleases", in Genetic Engineering, Principles and Methods, Vol. 6, pp. 117–140, Plenum Press (1984); Roberts, R. J. and Halford, S. E. in Nucleases [Eds. Linn, S. M., Lloyd, R. S., Roberts, R. J.] Cold Spring Harbor Press, pp 35–88 (1993)).

What is claimed is:

1. A method for identifying a restriction endonuclease using DNA methylase sequence motifs comprising the steps of:
   (a) screening a target DNA sequence for the presence of sequences known to encode DNA methylase sequence motifs;
   (b) identifying any open reading frames within about 3 Kb of the methylase sequence motifs screened in step (a);
   (c) expressing the open reading frames identified in step (b) to produce a protein product; and
   (d) assaying the protein product of step (c) for restriction endonuclease activity.

2. The method of claim 1, wherein the target DNA sequence is selected from the group consisting of bacterial DNA sequences, archaeal DNA sequences and viral DNA sequences.

3. The method of claim 1, wherein the screening of step(a) comprises searching DNA sequence databases.

4. The method of claim 1, wherein the protein products of step (c) comprises a translation mix which is produced by in vitro transcription and translation.

5. The method of claim 4, wherein the restriction endonuclease is a thermophilic restriction endonuclease and the translation mix is selected from the group consisting of a Wheat Germ translation mix, a bacterial S30, and a rabbit reticulocyte system.

6. The method of claim 1, wherein the protein products of step(c) are produced by recombinant DNA techniques.

7. The method of claim 1, wherein step (d) further comprises the steps of:
   (e) growing a microorganism which contains the target DNA sequence;
   (f) preparing cell extracts; and
   (g) testing the extracts of step (f) for restriction endonuclease activity.

8. The method of claim 1, wherein the methylase sequence motifs of step(a) are selected from the group consisting of cytosine-5 methylase motifs, N4C-methylase motifs, and N6A-methylase motifs.

* * * * *

UNITED STATES PATENT AND TRADEMARK OFFICE
CERTIFICATE OF CORRECTION

| | | |
|---|---|---|
| PATENT NO. | : 6,689,573 B1 | |
| APPLICATION NO. | : 09/577528 | |
| DATED | : February 10, 2004 | |
| INVENTOR(S) | : Richard D. Morgan et al. | |

It is certified that error appears in the above-identified patent and that said Letters Patent is hereby corrected as shown below:

Column 1, line 9, insert the following:

--Governmental Support

This invention was made with governmental support under SBIR Grant No. GM56535 awarded by the National Institutes of Health. The government has certain rights in this invention--.

Signed and Sealed this

Twenty-third Day of November, 2010

David J. Kappos
*Director of the United States Patent and Trademark Office*

SEQUENCE LISTING

<160> NUMBER OF SEQ ID NOS: 29

<210> SEQ ID NO 1
<211> LENGTH: 63
<212> TYPE: DNA
<213> ORGANISM: Methanococcus jannaschii

<400> SEQUENCE: 1
gtttaatacg actcactata gggttaggag gtattacata tggtgaaact tatgaaaaaa    60
ttg                                                                 63

<210> SEQ ID NO 2
<211> LENGTH: 38
<212> TYPE: DNA
<213> ORGANISM: Methanococcus jannaschii

<400> SEQUENCE: 2
gttggatccg caaaaagaa taggaatgga ttttaatg                             38

<210> SEQ ID NO 3
<211> LENGTH: 69
<212> TYPE: DNA
<213> ORGANISM: Haemophilus haemolyticus

<400> SEQUENCE: 3
taatacgact cactataggg aataattttg ttttaacttt aagaaggaga atgaaaatga    60
attggaaag                                                           69

<210> SEQ ID NO 4
<211> LENGTH: 22
<212> TYPE: DNA
<213> ORGANISM: Haemophilus haemolyticus

<400> SEQUENCE: 4
caattataaa gaaatagctg cc                                             22

<210> SEQ ID NO 5
<211> LENGTH: 64
<212> TYPE: DNA
<213> ORGANISM: Methanococcus jannaschii

<400> SEQUENCE: 5
gtttaatacg actcactata gggttaggag gtattacata tgagaaaaat gtttatttgt    60
ttgc                                                                64

<210> SEQ ID NO 6
<211> LENGTH: 31
<212> TYPE: DNA
<213> ORGANISM: Methanococcus jannaschii

<400> SEQUENCE: 6
gttggatccg gagattcctg aggcatcttt g                                   31

<210> SEQ ID NO 7
<211> LENGTH: 63
<212> TYPE: DNA
<213> ORGANISM: 'Axial Seamount' polynoid polychaete

<400> SEQUENCE: 7
gttggatcct aatacgactc actataggaa cagaccacca tggtggtaaa attggttaat    60
aac                                                                 63

<210> SEQ ID NO 8
<211> LENGTH: 36
<212> TYPE: DNA
<213> ORGANISM: Bacillus amyloliquefaciens

<400> SEQUENCE: 8
gttggatccg attgtagaaa gatttatcat taattc                             36

<210> SEQ ID NO 9
<211> LENGTH: 66
<212> TYPE: DNA
<213> ORGANISM: Methanococcus jannaschii

<400> SEQUENCE: 9
gtttaatacg actcactata gggttaggag gtattacata tgataaaatt tggagaagca   60
gttttg                                                              66

<210> SEQ ID NO 10
<211> LENGTH: 32
<212> TYPE: DNA
<213> ORGANISM: Methanococcus jannaschii

<400> SEQUENCE: 10
gttggatccg tgtaaagttt ttttgctggc tg                                 32

<210> SEQ ID NO 11
<211> LENGTH: 51
<212> TYPE: DNA
<213> ORGANISM: Methanococcus jannaschii

<400> SEQUENCE: 11
cctcctctag aagaaggaga tataccatgc cactaagtaa aaatgttata g             51

<210> SEQ ID NO 12
<211> LENGTH: 60
<212> TYPE: DNA
<213> ORGANISM: Methanococcus jannaschii

<400> SEQUENCE: 12
ggagggatcc tcgagcgctt gactgaatag ttatttttgc atatatttat tgtataattc   60

<210> SEQ ID NO 13
<211> LENGTH: 13
<212> TYPE: DNA
<213> ORGANISM: Streptomyces fimbriatus
<220> FEATURE:
<223> OTHER INFORMATION: At Position 5 through 9, "N" = G, A, C or T

<400> SEQUENCE: 13
ggccnnnnng gcc                                                      13

<210> SEQ ID NO 14
<211> LENGTH: 65
<212> TYPE: DNA
<213> ORGANISM: Methanococcus jannaschii

<400> SEQUENCE: 14
gttggatcct aatacgactc actataggaa cagaccacca tgaattttga atacatcatt   60
aacag                                                               65

<210> SEQ ID NO 15
<211> LENGTH: 33
<212> TYPE: DNA
<213> ORGANISM: Haemophilus influenzae

<400> SEQUENCE: 15
gttggatcca aattgaataa tggtatcatt cac       33

<210> SEQ ID NO 16
<211> LENGTH: 75
<212> TYPE: DNA
<213> ORGANISM: Pseudomonas alcaligenes

<400> SEQUENCE: 16
cgaaattaat acgactcact atagggagac cacaacggtt aaggaggtga caaaatgaag       60
aaaagtgcgt tagag       75

<210> SEQ ID NO 17
<211> LENGTH: 37
<212> TYPE: DNA
<213> ORGANISM: Pseudomonas alcaligenes

<400> SEQUENCE: 17
aaatggatcc agaattataa atacagtcta tcattac       37

<210> SEQ ID NO 18
<211> LENGTH: 59
<212> TYPE: DNA
<213> ORGANISM: Pseudomonas alcaligenes

<400> SEQUENCE: 18
gttggatcct aatacgactc actataggaa cagaccacca tgacgcaatg tccaaggtg       59

<210> SEQ ID NO 19
<211> LENGTH: 32
<212> TYPE: DNA
<213> ORGANISM: Pseudomonas alcaligenes

<400> SEQUENCE: 19
gttggatccg tcgacttggc aaagccctct tc       32

<210> SEQ ID NO 20
<211> LENGTH: 48
<212> TYPE: DNA
<213> ORGANISM: Pseudomonas alcaligenes

<400> SEQUENCE: 20
cctcctctag aagaaggaga tataccatga cgcaatgtcc aaggtgcc       48

<210> SEQ ID NO 21
<211> LENGTH: 35
<212> TYPE: DNA
<213> ORGANISM: Neisseria lactamica

<400> SEQUENCE: 21
ggagggatcc tcgagcgctt gactgaatag ttagg       35

<210> SEQ ID NO 22
<211> LENGTH: 49
<212> TYPE: DNA
<213> ORGANISM: Neisseria lactamica

<400> SEQUENCE: 22

-continued cctcctctag aagaaggaga tataccatga aaatcacaaa aacagaact          49

<210> SEQ ID NO 23
<211> LENGTH: 58
<212> TYPE: DNA
<213> ORGANISM: Methanococcus jannaschii

<400> SEQUENCE: 23
ggagggatcc tcgagcgctt gactgaatag tcatccgtta tcttcttcat ataatttc    58

<210> SEQ ID NO 24
<211> LENGTH: 6
<212> TYPE: PRT
<213> ORGANISM: Methanococcus jannaschii

<400> SEQUENCE: 24

Val Thr Ser Pro Pro Tyr
 1               5

<210> SEQ ID NO 25
<211> LENGTH: 11
<212> TYPE: PRT
<213> ORGANISM: Methanococcus jannaschii

<400> SEQUENCE: 25

Val Leu Asp Pro Phe Met Gly Ile Gly Ser Thr
 1               5                  10

<210> SEQ ID NO 26
<211> LENGTH: 51
<212> TYPE: DNA
<213> ORGANISM: Bacillus amyloliquefaciens

<400> SEQUENCE: 26
gttggatccg taattaagga ggtaattcat atggagataa ataaaatcta c           51

<210> SEQ ID NO 27
<211> LENGTH: 33
<212> TYPE: DNA
<213> ORGANISM: Streptomyces albus

<400> SEQUENCE: 27
gttgaatccg tcgactattt aaataaatgc atc                              33

<210> SEQ ID NO 28
<211> LENGTH: 61
<212> TYPE: DNA
<213> ORGANISM: Bacillus amyloliquefaciens

<400> SEQUENCE: 28
gttggatcct aatacgactc actataggaa cagaccacca tggatgataa gagctactat  60
g                                                                 61

<210> SEQ ID NO 29
<211> LENGTH: 27
<212> TYPE: DNA
<213> ORGANISM: Bacillus amyloliquefaciens

<400> SEQUENCE: 29
cattaatata taaataaata cataaat                                     27